(12) United States Patent
Graf et al.

(10) Patent No.: US 10,507,132 B2
(45) Date of Patent: Dec. 17, 2019

(54) TOPICAL ADMINISTRATION METHOD

(71) Applicant: NOVALIQ GMBH, Heidelberg (DE)

(72) Inventors: Gesche Graf, Bensheim (DE); Yasin Ahmed, Upminster Essex (GB); Stephanie Legner, Stuttgart (DE); Philip Kemp, Thatcham Berkshire (GB)

(73) Assignee: NOVALIQ GMBH, Heidelberg (DE)

( * ) Notice: Subject to any disclaimer, the term of this patent is extended or adjusted under 35 U.S.C. 154(b) by 0 days.

(21) Appl. No.: 16/312,855

(22) PCT Filed: Jun. 21, 2017

(86) PCT No.: PCT/EP2017/065163
§ 371 (c)(1),
(2) Date: Dec. 21, 2018

(87) PCT Pub. No.: WO2017/220625
PCT Pub. Date: Dec. 28, 2017

(65) Prior Publication Data
US 2019/0321218 A1 Oct. 24, 2019

(30) Foreign Application Priority Data

Jun. 23, 2016 (EP) .................................... 16176074
Jul. 19, 2016 (EP) .................................... 16180202
May 6, 2017 (EP) .................................... 17169837

(51) Int. Cl.
*A61F 9/00* (2006.01)
*A61P 27/04* (2006.01)
(Continued)

(52) U.S. Cl.
CPC .......... *A61F 9/0008* (2013.01); *A61K 9/0048* (2013.01); *A61K 31/02* (2013.01); *A61P 27/04* (2018.01)

(58) Field of Classification Search
CPC ..... A61F 9/0008; A61K 9/0048; A61K 31/02; A61P 27/04
See application file for complete search history.

(56) References Cited

U.S. PATENT DOCUMENTS 2,616,927 A 11/1952 Kauck et al.
5,077,036 A 12/1991 Long, Jr.
(Continued)

FOREIGN PATENT DOCUMENTS

EP 0 089 815 9/1983
EP 0593552 4/1994
(Continued)

OTHER PUBLICATIONS

Ahmed, et al., "Disposition of Timolol and Inulin in the Rabbit Eye Following Corneal Versus Non-Corneal Absorption," International Journal of Pharmaceutics, 1987, 38:9-21.
(Continued)

*Primary Examiner* — Benjamin J Klein
(74) *Attorney, Agent, or Firm* — Hoxie & Associates LLC

(57) ABSTRACT

The present invention relates to a method for topical administration of ophthalmic compositions in a dropwise manner, preferably for topical administration of ophthalmic compositions comprising semifluorinated alkanes (SFAs). Further, the present invention relates to the use of said methods in the prevention or treatment of ocular diseases or disorders or any symptoms or conditions associated therewith. In a further aspect, the present invention relates to a kit comprising a drop dispenser at least partially filled with a liquid composition for the use in such a method and directions for use of said drop dispenser.

17 Claims, 6 Drawing Sheets

(51) Int. Cl.
*A61K 31/02* (2006.01)
*A61K 9/00* (2006.01)

(56) References Cited

U.S. PATENT DOCUMENTS

| | | |
|---|---|---|
| 5,326,566 A | 7/1994 | Parab |
| 5,336,175 A | 8/1994 | Mames |
| 5,518,731 A | 5/1996 | Meadows |
| 5,667,809 A | 9/1997 | Trevino |
| 5,874,469 A | 2/1999 | Maniar et al. |
| 5,874,481 A | 2/1999 | Weers |
| 5,980,936 A | 11/1999 | Krafft et al. |
| 5,981,607 A | 11/1999 | Ding |
| 6,042,845 A | 3/2000 | Sun et al. |
| 6,060,085 A | 5/2000 | Osborne |
| 6,113,919 A | 9/2000 | Cronelus |
| 6,159,977 A | 12/2000 | Reeves |
| 6,177,477 B1 | 1/2001 | George et al. |
| 6,197,323 B1 | 3/2001 | Georgieff |
| 6,224,887 B1 | 5/2001 | Samour et al. |
| 6,262,126 B1 | 7/2001 | Meinert |
| 6,294,563 B1 | 9/2001 | Garst |
| 6,372,243 B2 | 4/2002 | Kobuch et al. |
| 6,391,879 B1 | 5/2002 | Reeves |
| 6,458,376 B1 | 10/2002 | Meadows |
| 6,486,212 B2 | 11/2002 | Meinert |
| 6,489,367 B1 | 12/2002 | Meinert |
| 6,730,328 B2 | 5/2004 | Maskiewicz |
| 7,001,607 B1 | 2/2006 | Menz |
| 7,026,359 B1 | 4/2006 | Gross |
| 7,258,869 B1 | 8/2007 | Berry |
| 7,740,875 B2 | 6/2010 | Dechow |
| 8,029,977 B2 | 10/2011 | Meinert et al. |
| 8,470,873 B2 | 6/2013 | Chen |
| 8,614,178 B2 | 12/2013 | Theisinger et al. |
| 8,916,157 B2 | 12/2014 | Krause et al. |
| 8,986,738 B2 | 3/2015 | Meinert |
| 9,241,900 B2 | 1/2016 | Wilson |
| 9,308,262 B2 | 4/2016 | Günther et al. |
| 9,757,459 B2 | 9/2017 | Theisinger et al. |
| 9,757,460 B2 | 9/2017 | Günther et al. |
| 9,770,508 B2 | 9/2017 | Günther et al. |
| 10,045,996 B2 | 8/2018 | Theisinger et al. |
| 2002/0004063 A1 | 1/2002 | Zhang |
| 2002/0128527 A1 | 9/2002 | Meinert |
| 2003/0018044 A1 | 1/2003 | Peyman |
| 2003/0027833 A1 | 2/2003 | Cleary et al. |
| 2003/0170194 A1 | 11/2003 | Piotrowiak |
| 2004/0044045 A1 | 3/2004 | Burk |
| 2004/0082660 A1 | 4/2004 | Ueno |
| 2004/0265362 A1 | 12/2004 | Susilo |
| 2004/0266702 A1 | 12/2004 | Dawson |
| 2005/0079210 A1 | 4/2005 | Gupta |
| 2005/0175541 A1 | 8/2005 | Lanza et al. |
| 2005/0274744 A1* | 12/2005 | Spada .......... A61F 9/0026 222/240 |
| 2005/0288196 A1 | 12/2005 | Horn |
| 2006/0153905 A1 | 7/2006 | Carrara et al. |
| 2008/0050335 A1 | 2/2008 | Faour et al. |
| 2008/0153909 A1 | 6/2008 | Dana et al. |
| 2008/0207537 A1 | 8/2008 | Turner et al. |
| 2008/0234389 A1 | 9/2008 | Mecozzi et al. |
| 2008/0260656 A1 | 10/2008 | Mallard |
| 2009/0149546 A1 | 6/2009 | Chang |
| 2010/0006600 A1* | 1/2010 | Dascanio .......... A61M 11/08 222/71 |
| 2010/0008996 A1 | 1/2010 | Meinert |
| 2010/0016814 A1* | 1/2010 | Gokhale .......... A61F 9/0008 604/298 |
| 2010/0226997 A1 | 9/2010 | Bowman et al. |
| 2010/0274215 A1 | 10/2010 | Wong et al. |
| 2011/0269704 A1 | 11/2011 | Seigfried |
| 2012/0010280 A1 | 1/2012 | Aleo et al. |
| 2012/0095097 A1 | 4/2012 | Tabuchi et al. |
| 2012/0238639 A1 | 9/2012 | Theisinger et al. |
| 2013/0046014 A1 | 2/2013 | Theisinger et al. |
| 2013/0084250 A1 | 4/2013 | Hagedorn et al. |
| 2013/0266652 A1 | 10/2013 | Theisinger et al. |
| 2013/0303473 A1 | 11/2013 | Wilson |
| 2014/0004197 A1 | 1/2014 | Theisinger et al. |
| 2014/0100180 A1 | 4/2014 | Günther et al. |
| 2014/0140942 A1 | 5/2014 | Günther et al. |
| 2014/0369993 A1 | 12/2014 | Günther et al. |
| 2015/0224064 A1 | 8/2015 | Günther et al. |
| 2015/0238605 A1 | 8/2015 | Günther et al. |
| 2016/0159902 A1 | 6/2016 | Günther et al. |
| 2017/0020726 A1* | 1/2017 | Labombarbe .......... B65D 1/0261 |
| 2017/0087100 A1 | 3/2017 | Scherer et al. |
| 2017/0087101 A1 | 3/2017 | Scherer et al. |
| 2017/0182060 A1 | 6/2017 | Wiedersberg et al. |

FOREIGN PATENT DOCUMENTS

| | | |
|---|---|---|
| EP | 0 670 159 | 9/1995 |
| EP | 0 965 329 | 12/1999 |
| EP | 0 965 334 | 12/1999 |
| EP | 1 152 749 | 11/2001 |
| EP | 0 939 655 | 6/2002 |
| EP | 2 110 126 | 10/2009 |
| EP | 2 332 525 | 6/2011 |
| EP | 2 335 735 | 6/2011 |
| EP | 2 462 921 | 6/2012 |
| JP | S6452722 | 2/1989 |
| JP | 2000511157 | 8/2000 |
| JP | 2001/158734 | 6/2001 |
| JP | 2008/505177 | 2/2008 |
| JP | 2011/006348 | 1/2011 |
| JP | 2011-024841 A | 2/2011 |
| WO | WO 1995/033447 | 12/1995 |
| WO | WO 96/40052 | 12/1996 |
| WO | WO 97/12852 A1 | 4/1997 |
| WO | WO 1998/005301 | 12/1998 |
| WO | WO 00/10531 | 3/2000 |
| WO | WO 00/024376 | 5/2000 |
| WO | WO 00/054588 | 9/2000 |
| WO | WO 02/49631 A1 | 6/2002 |
| WO | WO 2005/018530 | 3/2005 |
| WO | WO 2005/099718 | 10/2005 |
| WO | WO 2005/099752 | 10/2005 |
| WO | WO 2005/123035 | 12/2005 |
| WO | WO 2006/007510 | 1/2006 |
| WO | WO 2006/042059 | 4/2006 |
| WO | WO 2006/048242 | 5/2006 |
| WO | WO 2007/052288 | 5/2007 |
| WO | WO 2008/060359 | 5/2008 |
| WO | WO 2009/013435 | 1/2009 |
| WO | WO 2010/062394 | 6/2010 |
| WO | WO 2010/146536 | 12/2010 |
| WO | WO 2011/009436 | 1/2011 |
| WO | WO 2011/113855 | 3/2011 |
| WO | WO 2011/073134 | 6/2011 |
| WO | WO 2012/052418 | 4/2012 |
| WO | WO 2012/062834 | 5/2012 |
| WO | WO 2012/093113 | 7/2012 |
| WO | WO 2012/121754 | 9/2012 |
| WO | WO 2012/160179 | 11/2012 |
| WO | WO 2012/160180 | 11/2012 |
| WO | WO 2013/110621 | 8/2013 |
| WO | WO 2014/041055 | 3/2014 |
| WO | WO 2014/041071 | 3/2014 |
| WO | WO 2014/154531 | 10/2014 |
| WO | WO 2015/011199 | 1/2015 |
| WO | WO 2016/025560 A1 | 2/2016 |
| WO | WO 2018/115097 | 6/2018 |

OTHER PUBLICATIONS

Baerdemaeker, "Pharmacokinetics in Obese Patients," Continuing Education in Anesthesia, Critical Care & Pain, 2004, 4:152-155.
Barata-Vallejo et al., "(Me$_3$Si)$_3$SiH-Mediated Intermolecular Radical Perfluoroalkylation Reactions of Olefins in Water," J. Org. Chem., 2010, 75:6141-6148.

(56) References Cited

OTHER PUBLICATIONS

Bardin et al., "Long-Range Nanometer-Scale Organization of Semifluorinated Alkane Monolayers at the Air/Water Interface," Langmuir, 2011, 27:13497-13505.
Blackie et al., "MGD: Getting to the Root Cause of Dry Eye", Review of Optometry, 2012, pp. 1-12.
Broniatowski, M. et al., "Langmuir Monolayers Characteristics of (Perfluorodecyl)-Alkanes," Journal of Physical Chemistry B, 2004, 108:13403-13411.
Chemical Book, "5-Fluorouracil," available at http://www.chemicalbook.com/-ChemicalProductProperty_EN_CB8162744.htm>, accessed Mar. 7, 2014, 1 page.
Chhadva et al., "Meibomian Gland Disease the Role of Gland Dysfunction in Dry Eye Disease," Ophthalmology (2017) 124(11 Supplement): S20-S26.
Costa Gomes et al., "Solubility of dioxygen in seven fluorinated liquids," Journal of Fluorine Chemistry, 2004, 125:1325-1329.
Davies, "Biopharmaceutical Considerations in Topical Ocular Drug Delivery," Clin. Exper. Pharmacol. Physiol., 2000, 27:558-562.
Dembinski et al., Semi-fluorinated Alkanes as Carriers for Drug Targeting in Acute Respiratory Failure, Experimental Lung Research, 2010, 36(8):499-507.
Dias et al., "Solubility of oxygen in liquid perfluorocarbon," Fluid Phase Equilibria, 2004, 222-223:325-330.
Elkeeb et al., "Transungual Drug Delivery: Current Status," Int J Pharmaceutics, 2010, 384:1-8.
English-language machine translation of EP0670159 (A1) issued in U.S. Appl. No. 14/122,025 on Apr. 1, 2015, 10 pages.
Freiburger Dokumentenserver (FreiDok), Albert-Ludwigs, Unversitat Feiburg im Breisgau, retrieved from the Internet, date accessed: Feb. 5, 2014, 2 pages URL: <http://www.freidok.uni-freiburg.de/volltexte/5682>.
Gayton, J., "Etiology, Prevalence, and Treatment of Dry Eye Disease," Clinical Ophthalmology, 2009,3:405-412.
Gehlsen et al., "A semifluorinated alkane (F4H5) as novel carrier for cyclosporine A: a promising therapeutic and prophylactic option for topical treatment of dry eye," Graefe's Arch. Clin. Exp. Ophthalmol., (2017) 255(4):767-775.
Gehlsen, U., et al., "Cyclosporine A using F4H5 as liquid drug carrier is effective in treating experimental dry-eye disease," Investigative Ophthalmology & Visual Science, 2015, 56(319), Abstract Only (2 pages).
Gerdenitsch, "Emulsions—established and promising drug carriers for parenteral administration", retrieved from Internet, date accessed: Jun. 20, 2016, 2 pages URL: <http:/ipimediaworld.com/wp-content/uploads/2012/05/Pages-from-IPI-Volume-2-Issue-1-11.pdf.>.
German, E.J., et al., "Reality of drop size from multi-dose eye drop bottles: is it cause for concern?" Eye, 1999, 13:93-100.
Gopal et al., "Use of intravitreal injection of triamcinolone acetonide in the treatment of age-related macular degeneration," Indian J Ophthalmol., 2007, 55(6):431-435, (8 pages).
Griffin, W., "Classification of Surface-Active Agents by 'HLB'," Journal of the Society of Cosmetic Chemists,1949, 1:311-326.
Hardung, H., "Semifluorierte und perfluorierte Vergindungen zur topischen und parenteralen Anwendung," 2008, 188 pages, retrieved from Internet, date accessed: Oct. 10, 2011, URL: <http://www.freidok.uni-freiburg.de/volltexte/5682/pdf/Dissertation_Hardung.pdf>.
Hardung, H., "Semifluorierte und perfluorierte Verbindungen zur topischen und parenteralen Anwendung," 2008, English Language Abstract, 2 pages, retrieved from https://freidok.uni-freiburg.de/data/5682 (retrieved on Jul. 10, 2017).
Hoerauf et al., "Combined Use of Partially Fluorinated Alkanes, Perfluorocarbon Liquids and Silicone Oil: An Experimental Study," Graefe's Archive for Clinical and Experimental Ophthalmology, 2001, 239(5):373-381.
Holm, R. et al., "A novel excipient, 1-perfluorohexyloctane shows limited utility for the oral delivery of poorly water-soluble drugs," European Journal of Pharmaceutical Sciences, 2011, 42: 416-422.
International Preliminary Report on Patentability dated Sep. 18, 2012, for International Patent Application PCT/EP2011/053949, 9 Pages.
International Preliminary Report on Patentability dated Apr. 23, 2013, for International Patent Application PCT/EP2011/068141, 4 Pages.
International Preliminary Report on Patentability dated May 14, 2013, for International Patent Application PCT/EP2011/069795, 8 Pages.
International Preliminary Report on Patentability dated Jul. 10, 2013, for International Patent Application PCT/EP2012/050043, 5 Pages.
International Preliminary Report on Patentability dated Nov. 26, 2013, for International Patent Application PCT/EP2012/059787, 9 Pages.
International Preliminary Report on Patentability dated Nov. 26, 2013, for International Patent Application PCT/EP2012/059788, 8 Pages.
International Preliminary Report on Patentability dated Jul. 29, 2014, for International Application No. PCT/EP2013/051163, 7 pages.
International Preliminary Report on Patentability dated Mar. 17, 2015, for International Application No. PCT/EP2013/068882, 5 pages.
International Preliminary Report on Patentability dated Mar. 17, 2015, for International Application No. PCT/EP2013/068909, 7 pages.
International Preliminary Report on Patentability dated Jan. 26, 2016, for International Application No. PCT/EP2014/065840, 11 pages.
International Search Report for International Application No. PCT/EP2011/053949 dated Sep. 6, 2011, 5 pages.
International Search Report for International Application No. PCT/EP2011/068141 dated Dec. 14, 2011, 2 pages.
International Search Report for International Patent Application PCT/EP2011/069795 dated Jan. 16, 2012, 3 pages.
International Search Report for International Patent Application PCT/EP2012/050043 dated Apr. 24, 2012, 2 pages.
International Search Report for International Application No. PCT/EP2012/059787 dated Dec. 5, 2012, 4 pages.
International Search Report for International Application No. PCT/EP2012/059788 dated Dec. 3, 2012, 4 pages.
International Search Report for International Application No. PCT/EP2013/051163 dated Mar. 4, 2013, 4 pages.
International Search Report for International Application No. PCT/EP2013/068882 dated Oct. 30, 2013, 4 pages.
International Search Report for International Application No. PCT/EP2013/068909 dated Dec. 5, 2013, 4 pages.
International Search Report for International Application No. PCT/EP2014/065840 dated Oct. 7, 2014, 4 pages.
International Search Report for International Application No. PCT/EP2016/073262 dated Nov. 18, 2016, 5 pages.
International Search Report for International Application No. PCT/EP2016/073263 dated Dec. 23, 2016, 3 pages.
International Search Report for International Application No. PCT/EP2017/083770 (revised version) dated Jul. 6, 2018, 4 pages.
International Search Report for International Application No. PCT/EP2017/065163 dated Aug. 8, 2017, 3 pages.
International Search Report and Written Opinion for International Application No. PCT/EP2017/083770 dated Jul. 6, 2018, 14 pages.
Ishizaki et al., "Treatment of Diabetic Retinopathy", Forum: Complication, Practice, 2009, 26(5): 474-476 (3 pages).
Jonas et al., "Intravitreal triamcinolone acetonide for exudative age-related macular degeneration," Br J Ophthalmol, 2003, 87:462-468.
Joussen et al., "The concept of heavy tamponades—chances and limitations," Graefes Arch Exp Ophthalmol, 2008, 246:1217-1224.
JP 2000511157A, English Machine Translation of the Abstract, Description, and Claims, Espacenet, Date Accessed: Feb. 10, 2016, 15 pages.
JPS6452722, English Machine Translation of the Abstract, Description, and Claims, Espacenet, Date Accessed: Feb. 10, 2016, 4 pages.

(56) References Cited

OTHER PUBLICATIONS

Kaercher et al., "NovaTears® as new Therapy in Dry Eye Results from three prospective, multicenter, non-interventional studies in different patient populations", TFOS Conference (Tear Film & Ocular Surface), Sep. 7-10, 2016, Montpellier, France, Poster Session II, Poster No. 60, 1 page.
Knepp et al., "Stability of Nonaqueous Suspension Formulations of Plasma Derived Factor IX and Recombinant Human Alpha Interferon at Elevated Temperatures," Pharmaceutical Research, 1998, 15 (7):1090-1095.
Kociok, N., "Influence on Membrane-Mediated Cell Activation by Vesicles of Silicone Oil or Perfluorohexyloctane," Graefe's Archive for Clinical and Experimental Ophthalmology, 2005, 243, 345-358.
Lemp, M., "Management of Dry Eye Disease", The American Journal of Managed Care, 2008, 14(3):S88-S101.
Lin, H. et al., "Thy eye disease: A review of diagnostic approaches and treatments," Saudi Journal of Ophthalmology, 2014, 28:173-181.
Mackiewicz, J. et al., "In Vivo Retinal Tolerance of Various Heavy Silicone Oils," Investigative Ophthalmology & Visual Science, 2007, 48 (4):1873-1883.
Mantle et al., "Adverse and Beneficial Effect of Plant Extracts on Skin Disorders," Adverse Drug Reaction and Toxicological Reviews, Oxford University Press, 2001, 20(2):89-103.
Meinert, H. et al., "The Use of Semifluorinated Alkanes in Blood-Substitutes," Biomaterials, Artificial Cells, and Immobilization Biotechnology, 1993, 21 (5), 583-595.
Meinert, H. et al., "Semifluorinated Alkanes—A New Class of Compounds with Outstanding Properties for Use in Ophthalmology," European Journal of Ophthalmology, 2000, 10(3), 189-197.
Messmer et al., "Semifluorierte Alkane als Therapie bei Meibomdrüsen-Dysfunktion Ergebnisse einer prospektiven, multizentrischen Beobachtungsstudie", Presentation, DOG-Kongress, Sep. 29-Oct. 2, 2016, Berlin DOG (Deutsche Ophtalmologische Gesellschaft), Poster No. PSa03-02, 1 page (German language version).
Messmer et al., "Semifluorinated Alkanes as a Therapy for Meibomian Gland Dysfunction Results of a prospective, multi-centered observational study", Presentation, DOG-Kongress, Sep. 29, 2016-Oct. 2, 2016, Berlin DOG (Deutsche Ophtalmologische Gesellschaft), Poster No. PSa03-02, English Translation, 6 pages.
Messmer et al. "Semifluorinated Alkanes as a Therapy for Meibomian Gland Dysfunction Results of a prospective, multi-centered observational study", Presentation, DOG-Kongress, Sep. 29, 2016-Oct. 2, 2016, Berlin DOG (Deutsche Ophtalmologische Gesellschaft), Ophthalmologe, Aug. 2016 Poster No. PSa03-02, English Translation of Abstract, p. 138.
Messmer, E.M., "The Pathophysiology, Diagnosis, and Treatment of Dry Eye Disease," (2015) Deutsches Arzteblatt International, 112(5):71-82.
Murdan, S., "Enhancing the Nail Permeability of Topically Applied Drugs," Expert Opinion on Drug Delivery, 2008, 5(11), 1267-1282.
O'Ourke, M. et al., "Enhancing Delivery of Topical Ocular Drops," Cataract & Refractive Surgery Today Europe, 2016, 2 pages.
Perry, "Dry Eye Disease: Pathophysiology, Classification, and Diagnosis," The American Journal of Managed Care, 2008, 14(3): S79-S87.
Pflugfelder et al., "The Pathophysiology of Dry Eye Disease What We Know and Future Directions for Research," Ophthalmology (2017) 124(11 Supplement): S4-S13.
Pinarci, E. et al., "Intraocular Gas Application in the Diagnosis and Treatment of Valsalva Retiopathy in Case with Premacular Hemorrhage," XP002625604, Retina Vitreus, 2009, 17 (2):153-155, 1 page, abstract only.
Plassmann, M. et al., "Trace Analytical Methods for Semifluorinated n-Alkanes in Snow, Soil, and Air," Analytical Chemistry, 2010, 82(11):4551-4557.

Plassmann, M. et al., "Theoretical and Experimental Simulation of the Fate of Semifluorinated n-Alkanes During Snowmelt," Environmental Science & Technology, 2010, 44(17):6692-6697.
Rosca-Casian, O. et al., "Antifungal Activity of *Aloe vera* Leaves," Fitoterapia, 2007, 28:219-222.
Rosenberg, A.S., "Effects of Protein Aggregates: An Immunologic Perspective," The AAPS Journal, 2006, 8 (3):E501-E507.
Sall, K. et al. "Two Multicenter, Randomized Studies of the Efficacy and Safety of Cyclosporine Ophthalmic Emulsion in Moderate to Severe Dry Eye Disease," Ophthalmology, 2000, 107(4):631-639.
Sato et al., "Vitrectomy and Intraocular Lens Implantation for Cytomegalovirus Retinitis in a Patient with Acquired Immunodeficiency Syndrome," Presented by Medical Online, New Ophthalmology, 1999, 16(7): 995-998 (4 pages).
Schmutz et al., "Fluorinated Vesicles Made from Combinations of Phospholipids and Semifluorinated Alkanes. Direct Experimental Evidence of the Location of the Semifluorinated Alkane within the Bilayer," Langmuir, 2003, 19:4889-4894.
Schnetler et al., "Lipid composition of human meibum: a review," S Afr Optom, 2013, 72(2), 86-93.
Spöler et al., "Towards a New in vitro Model of Dry Eye: The ex vivo Eye Irritation Test," Developments in Ophthalmology, 2010, 45, 93-107.
Steven, P. et al. "Semifluorinated Alkane Eye Drops for Treatment of Dry Eye Disease—A Prospective, Multicenter Noninterventional Study" Journal of Ocular Pharmacology and Therapeutics (2015) vol. 31(8):498-503.
Steven et al., "Semifluorinated Alkane Eye Drops for Treatment of Dry Eye Disease Due to Meibomian Gland Disease," Journal of Ocular Pharmacology and Therapeutics, 2017, 33(9):1-8.
Stevenson, C., "Characterization of Protein and Peptide Stability and Solubility in Non-Aqueous Solvents," Current Pharmaceutical Biotechnology, 2000, 1:165-182.
Thomas et al., "The therapeutic uses of topical vitamin A acid," Journal of the American Academy of Dermatology, 1981, 4(5): 505-513.
Tiffany, J.M., "Individual Variations in Human Meibomian Composition," Exp. Eye Res., 1978, 27, 289-300.
Troiano et al., "Effect of Hypotonic .4% Hyaluronic Acid Drops in Dry Eye Patients: A Cross-Study", Cornea 27(10): 1126-1130, 1 page (Abstract Only).
Ujiie et al., "Successful Treatment of Nail Lichen Planus with topical Tacrolimus", Department of Dermatology, Nov. 4, 2009, 2 pages.
Wang, W., "Lyophilization and Development of Solid Protein Pharmaceuticals," International Journal of Pharmaceutics, 2000, 203, 1-60.
"What is retinal vitrectomy?" Presented by: Medical Online, Obesity and Diabetes Mellitus, 2005, 4(2): 284-286, 3 pages.
Wong et al., "Perfluorocarbon and Semifluorinated Alkanes," Seminars in Ophthalmology; vol. 15 (1), 2000, p. 25-35.
Xalatan, Latanoprost Ophthalmic Solution, 50 μg/mL Prostaglandin $F_{2\alpha}$ analogue, Product Monograph, Jul. 21, 2014, 30 pages.
Yaoxue Zhuanye Zhishi II (Editor: Jin Xiangqun), Military Medical Science Press, 1st Printing of 2nd Edition, Mar. 2009, p. 158.
Yaoxue Zhuanye Zhishi II (Editor: Jin Xiangqun), Military Medical Science Press, 1st Printing of 2nd Edition, Mar. 2009, p. 158, 3 pages (English Machine Translation).
Zakeri et al., "Topical calcipotriol therapy in nail psoriasis", A study of 24 cases, Dermatology Online Journal, 2005, 2 pages.
Zhang et al., "Surface micelles of semifluorinated alkanes in Langmuir-Blodgett monolayers," Phys. Chem. Chem. Phys., 2004, 6:1566-1569.
English Translation of Notice of Reasons for Refusal, Issued in Japanese Application No. 2018-566545, dated Jul. 5, 2019, 4 pages.

\* cited by examiner

TOPICAL ADMINISTRATION METHOD

CROSS-REFERENCE TO RELATED APPLICATIONS

This application is a U.S. national stage application filed under 35 U.S.C. § 371 of International Application No. PCT/EP2017/065163, filed on Jun. 21, 2017, which claims priority to, and the benefit of, European Application No. 16176074.9, filed Jun. 23, 2016, and European Application No. 16180202.0, filed Jul. 19, 2016, and European Application No. 17169837.6, filed May 6, 2017, the contents of each of which are incorporated herein by reference in their entireties.

FIELD

The present invention relates to a method for topical administration of ophthalmic compositions in a dropwise manner, preferably for topical administration of ophthalmic compositions comprising semifluorinated alkanes (SFAs). Further, the present invention relates to the use of said methods in the prevention or treatment of ocular diseases or disorders or any symptoms or conditions associated therewith. In a further aspect, the present invention relates to specific designs of a drop dispenser and to a kit comprising a drop dispenser at least partially filled with a liquid composition for the use in such a method and directions for use of said drop dispenser.

BACKGROUND

Semifluorinated alkanes (SFAs) are linear or branched compounds composed of at least one non-fluorinated hydrocarbon segment and at least one perfluorinated hydrocarbon segment. Semi-fluorinated alkanes have been described for various applications, for example commercially for unfolding and reapplying a retina, for long-term tamponade as vitreous humour substitute (H. Meinert et al., European Journal of Ophthalmology, Vol. 10(3), pp. 189-197, 2000), and as wash-out solutions for residual silicon oil after vitreo-retinal surgery.

WO2011/073134 discloses solutions of cyclosporine in semifluorinated alkanes of the formula $CF_3(CF_2)_n(CH_2)_mCH_3$, optionally in the presence of a co-solvent such as ethanol, wherein the semifluorinated alkane functions as a liquid drug delivery vehicle for cyclosporine for topical treatment of keratoconjunctivitis sicca.

WO2014/041055 describes mixtures of semifluorinated alkanes of the formula $CF_3(CF_2)_n(CH_2)_mCH_3$. These mixtures are described to be ophthalmically applicable as tear film substitutes or for treating patients with dry eye syndrome and/or meibomian gland dysfunction.

It is known that the volume of drug instilled into the eye is of particular importance as it is one of the sources of drug response variation (German E. J. et. al, Eye 1999, 93-100).

Conventional eye drops are usually water-based compositions. When administering such water-based eye drops to the eye, the patient usually inverts the (eye-)dropper bottle that holds the ophthalmic composition and exerts a pressuring force to the flexible bottle in order to force one or more drops to be released from the (eye-)dropper bottle. This is usually done by simply squeezing the inverted eyedropper bottle resulting in the release of one or more drops (the aforementioned method is referred to as "pressure method" throughout this document).

Said conventional administration method (pressure method) known from water-based ophthalmic compositions is not suitable or not reliably suitable for administering ophthalmic compositions comprising SFAs, since SFA-comprising drops may be released from the eyedropper in a rather uncontrolled manner. Without being bound by theory, this is attributed to the interplay of the special surface properties of the amphiphilic SFAs, namely the interplay of high spreading capabilities, high density and/or low surface tension.

Furthermore, also an administration method that relies only on the inversion of the (eye-) dropper bottle without exerting a pressuring force to the bottle (the aforementioned method is referred to as "inversion method" throughout this document) is not suitable or not reliably suitable for administering ophthalmic compositions comprising SFAs, since SFA-comprising drops are also released from the eyedropper in a highly uncontrolled manner employing said inversion method. Again, this is attributed to the interplay of the special surface properties of the amphiphilic SFAs, namely the interplay of high spreading capabilities, high density and/or low surface tension.

Thus, it is an object of the present invention to establish a reliable method for the controlled administration, preferably for the controlled topical administration of compositions comprising semifluorinated alkanes (SFAs) to the eye in a drop-by-drop manner.

SUMMARY OF THE INVENTION

In a first aspect, the invention relates to a method for dropwise topical administration of a liquid composition (2), comprising the steps of:
a) providing a drop dispenser (1), comprising
  a container part (1B) with an interior volume partially filled with the liquid composition (2) and a gaseous phase (3) filling the remainder of the interior volume at ambient pressure, the container part (1B) having a displaceable section (1C) and optionally a substantially stationary section, and
  a dropper part (1A) in physical connection and in fluid communication with the interior volume of the container part (1B), comprising an outflow channel (5), connecting the interior volume of the container part (1B) to the environment;
b) exerting a first force to the displaceable section (1C) of the container part (1B) of the drop dispenser (1) while holding the drop dispenser (1) in an upright position in which the outflow channel (5) is not in contact with the liquid composition (2), thereby reducing the interior volume of the container part (1B) and forcing the gaseous phase (3) of the interior volume at least partially out of the drop dispenser (1) into the environment;
c) inverting the drop dispenser (1) to an inverted position in which the liquid composition (2) is in contact with the outflow channel (5);
d) releasing said first force from the displaceable section (1C) of the container part (1B) at least partly, thereby reducing the pressure inside the container part (1B) below ambient pressure; and
e) exerting a second force to the displaceable section (1C) of the container part (1B), while still holding the drop dispenser in the inverted position in which the liquid composition (2) is in contact with the outflow channel (5), thereby raising the pressure inside the interior volume of the container part (1B) above ambient pressure and releasing the liquid composition (2) dropwise from the dropper part (1A) of the drop dispenser (1).

In a second aspect, the invention relates to the use of a method according to the first aspect of the invention for preventing or treating an ocular disease or disorder or any symptoms or conditions associated therewith.

In a third aspect, the invention relates to a method of treating an ocular disease or disorder or any symptoms or conditions associated therewith, comprising dropwise administration of a liquid ophthalmic composition according to the method according to the first aspect of the invention.

In a fourth aspect, the present invention relates to a drop dispenser (1), comprising
- a container part (1B) with an interior volume partially filled with the liquid composition (2) and a gaseous phase (3) filling the remainder of the interior volume at ambient pressure, the container part (1B) having a displaceable section (1C) and optionally a substantially stationary section, and
- a dropper part (1A) in physical connection and in fluid communication with the interior volume of the container part (1B), comprising an outflow channel (5), connecting the interior volume of the container part (1B) to the environment; wherein at least a portion of the outflow channel (5) has an inner diameter in the range of 0.09 to 0.19 mm.

In a fifth further aspect, the invention relates to a kit comprising
- a drop dispenser (1) at least partially filled with a liquid composition (2) and a gaseous phase (3) for the use in a method according to the first aspect of the invention and
- directions for use of the drop dispenser (1) in a method according to the first aspect of the invention.

Surprisingly, it was found that the administration of drops or droplets of compositions comprising semifluorinated alkanes to the eye is preferably performed utilizing an underpressure in the (eye-)dropper bottle. By generating an underpressure in the interior volume of the dropper bottle, uncontrolled release of said compositions comprising semifluorinated alkanes contained in the dropper bottle is effectively prevented and reliable administration of said compositions in a dropwise manner is safeguarded. This allows for reproducible dosing of compositions comprising SFAs to the eye, including compositions comprising pharmaceutical active ingredients as well as compositions comprising no pharmaceutical active ingredients. The reliable administration is especially important to the administration of therapeutic compositions comprising semifluorinated alkanes since the corresponding drop volumes (approximately in the range of 5 to 15 µl, in many cases in the range of 8 to 15 µl) are much smaller (as compared to aqueous eye drops) and are thus more prone to overdosing or dose variation.

Further, the inventors found that the method of the present invention, employing an underpressure in the dropper bottle, not only works for compositions comprising SFAs, but also for conventional water-based ophthalmic compositions. Thus, the inventors of the present invention surprisingly found a universal administration method for ophthalmic compositions, including water-free (e.g. SFA-based) or water-based compositions. By using the method of the first aspect of the present invention (said method is also referred to as "underpressure method" throughout this document) ophthalmic compositions can be administered to the eye in a highly-controlled fashion, which safeguards the reliably and reproducibly administration of a defined dose of said ophthalmic compositions to the eye.

Even further, the inventors found that the method according to the first aspect of the present invention, employing an underpressure, works reliable also below ambient temperature, namely with ophthalmic compositions that were stored below ambient temperature (e.g. refrigerated compositions), which is problematic when using the pressure method as well as the inversion method, especially in the case of SFA-based compositions. Employing the present invention, said compositions may be directly administered without the need to equilibrate the composition to ambient temperature before use. The method according to the first aspect of the present invention (underpressure method) also works regardless of the volume of the headspace (gaseous volume that fills the remainder of the interior volume of the dropper bottle in addition to the liquid (ophthalmic) composition) in the dropper bottle. During ongoing use of the composition, the volume of the headspace is continuously increasing, as the volume of the liquid ophthalmic composition is decreasing. Such increasing headspace volume hampers reliable administration of ophthalmic compositions utilizing the pressure method or inversion method, especially when SFA-based compositions are employed—which is not the case when the underpressure method according the present invention is employed.

DETAILED DESCRIPTION OF THE INVENTION

Figure 1:
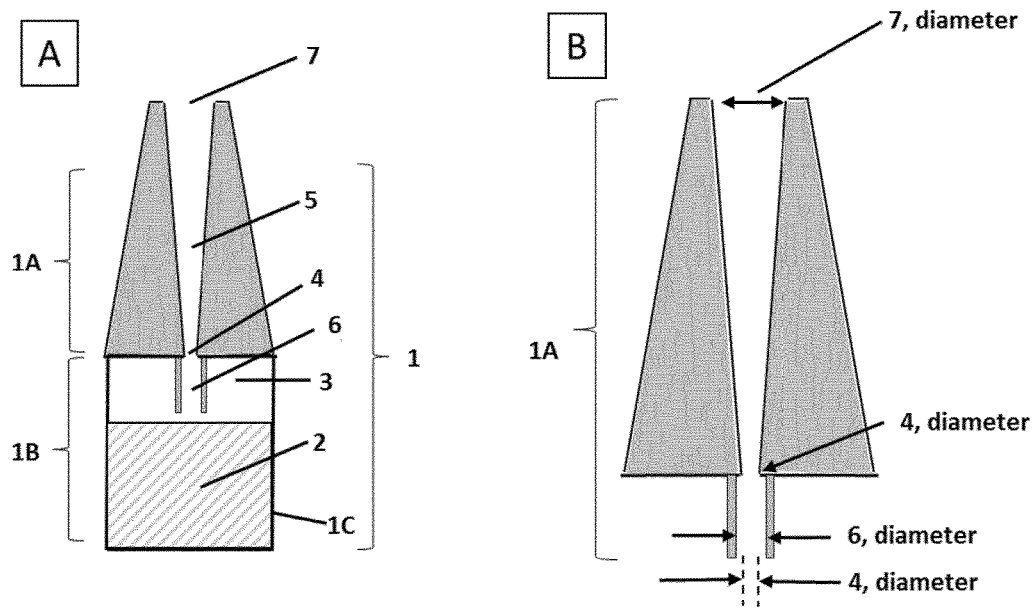
FIG. 1(A): Schematic representation of a drop dispenser (dropper bottle) (1) in the upright position
FIG. 1(B): Schematic representation of a dropper part (1A)
Figure 2:
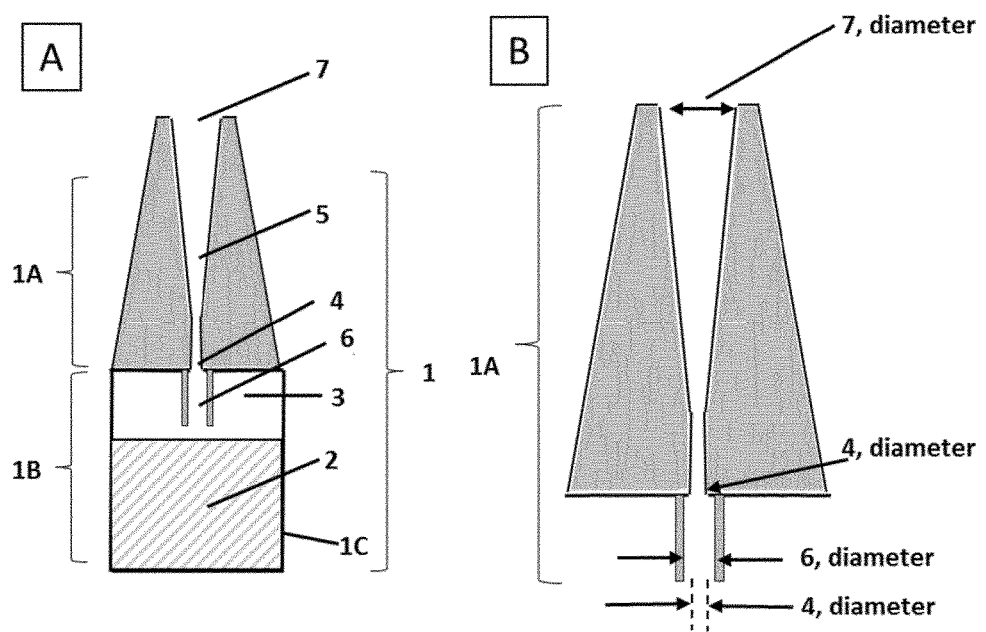
FIG. 2(A): Schematic representation of a slightly different configuration of a drop dispenser (1) in the upright position
FIG. 2(B): Schematic representation of a dropper part (1A)
Figure 3:
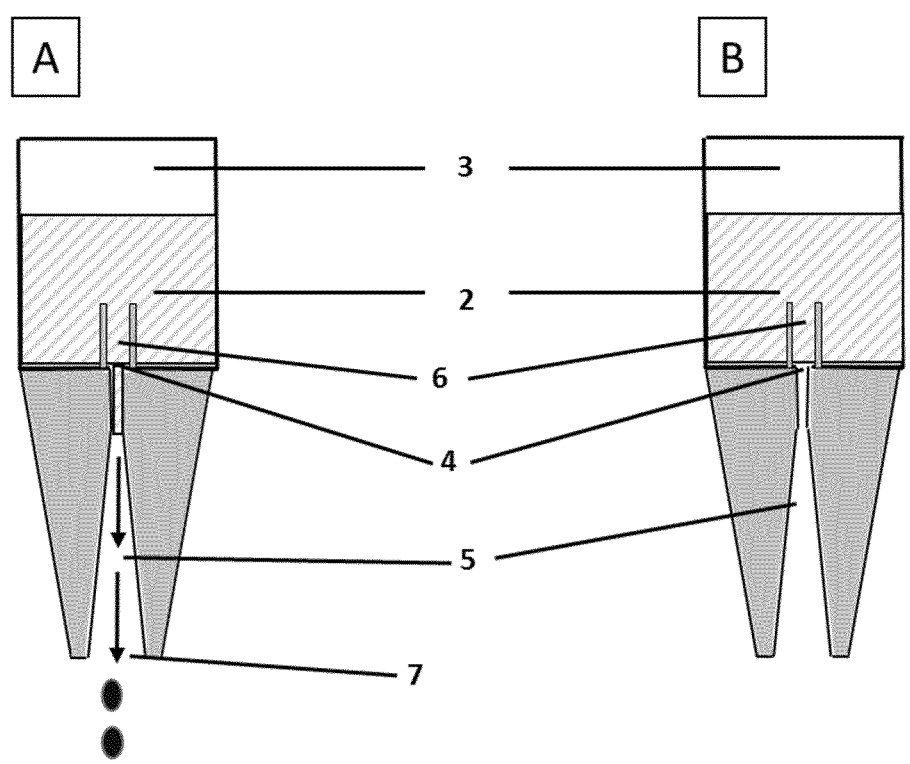
FIG. 3(A): Schematic representation of a drop dispenser (dropper bottle) (1) in the inverted (downside) position
FIG. 3(B): Schematic representation of a drop dispenser (dropper bottle) (1) in the inverted (downside) position

The terms "consist of", "consists of" and "consisting of" as used herein are so-called closed language meaning that only the mentioned components are present. The terms "comprise", "comprises" and "comprising" as used herein are so-called open language, meaning that one or more further components may or may not also be present.

The term "active pharmaceutical ingredient" (also referred to as "API" throughout this document) refers to any type of pharmaceutically active compound or derivative that is useful in the prevention, diagnosis, stabilization, treatment, or—generally speaking—management of a condition, disorder or disease.

The term "therapeutically effective amount" as used herein refers to a dose, concentration or strength which is useful for producing a desired pharmacological effect.

According to the first aspect the present invention provides a method for dropwise topical administration of a liquid composition (2), comprising the steps a) to e) which will be described in further detail below.

The term "dropwise" as used herein means that a liquid, more specifically the liquid composition of the present invention is provided in a drop-by-drop fashion, which means that one discrete drop, irrespective of its size or volume, is provided or administered at a time and/or that a plurality of drops or droplets, preferably of the liquid composition, is provided in a consecutive manner, one at a time.

Further, according to the present invention, dropwise administration of the liquid composition is performed topically, meaning on the surface, e.g. to the skin or other outer boundary of a human or animal body or any part thereof. Preferably, the liquid composition is topically administered to the eye surface or an eye tissue.

The term "liquid composition" according to the present invention means any water-containing or water-free liquid, solution, emulsion or dispersion, preferably a liquid solution that may be applied to the human or animal body and that may optionally contain one or more active pharmaceutical ingredient (API) as defined above or further compounds like excipients, may optionally contain one or more active pharmaceutical ingredient (API) as defined above or further compounds like excipients, such as organic solvents, lipids, oils, lipophilic vitamins, lubricants, viscosity agents, acids, bases, antioxidants, stabilizers, synergists, coloring agents, thickening agents,—and if required in a particular cases—a preservative or a surfactant and mixtures thereof.

Potentially useful organic solvents include, but are not limited to, glycerol, propylene glycol, polyethylene glycol, ethanol, acetone, ethyl acetate, isopropyl alcohol, pentylene glycol, liquid paraffin, triglyceride oils and hydrofluorocarbons.

Potentially useful lipids or oily excipients include, but are not limited to, triglyceride oils (e.g. soybean oil, olive oil, sesame oil, cotton seed oil, castor oil, sweet almond oil), mineral oil (e.g. petrolatum and liquid paraffin), medium chain triglycerides (MCT), oily fatty acids, isopropyl myristate, oily fatty alcohols, esters of sorbitol and fatty acids, oily sucrose esters, oily cholesterol esters, oily wax esters, glycerophospholipids, sphingolipids, or any oily substance which is physiologically tolerated by the eye.

Potentially useful antioxidants include, but are not limited to, vitamin E or vitamin E derivatives, ascorbic acid, sulphites, hydrogen sulphites, gallic acid esters, butyl hydroxyanisole (BHA), butyl hydroxytoluene (BHT) or acetylcysteine.

According to step a) of the administration method according to the first aspect of the present invention a drop dispenser (1) is provided. A "drop dispenser" as used herein may be a container, dispenser, applicator or bottle of any suitable kind for handheld use which can hold at least a single dose, preferably multiple doses of the liquid composition and which may be designed of a single piece or multiple pieces or parts and which may typically be made of a material which is essentially inert against the liquid composition to be administered and which may be rigid such as glass (especially when used in a combination with a flexible material) or preferably flexible, such as, for example polyethylene or polypropylene. In a preferred embodiment of the present invention the container part (1B) of the drop dispenser (1) is at least partially made of a flexible polymer, preferably of a flexible thermoplastic polymer.

The drop dispenser provided in step a) of the present invention comprises a container part (1B) and a dropper part (1A). The "container part" is the portion of the drop dispenser which holds the liquid composition to be administered dropwise in the amount of a single dose, preferably however in an amount of multiple doses or drops, typically in an amount of 0.1 to 15 ml, more typically in an amount of 0.1 to 10 ml, even more typically in an amount of 0.1 to 5 ml. The container part holds an interior space or volume which is at least partially filled with the liquid composition to be administered. The container part (1B) also holds a gaseous phase (3) which fills the remainder of the interior volume which is not filled with the liquid composition (2). The gaseous phase typically consists of air or a protective gas or a mixture of air and a protective gas or a mixture of different protective gases and evaporated portions or traces of the components of the liquid composition (2). According to step a) of the present method the gaseous phase (3) as well as the liquid composition (2) is held under ambient pressure, which means that it is under the same pressure as the surrounding atmospheric pressure, at least after the container has been opened.

The container part (1B) of the drop dispenser according to step a) has a displaceable section (1C) and optionally a substantially stationary section. The term "displaceable section" as used herein may be any portion or area of the container part (1B) that may be displaced out of its original position relative to a fixed portion of the drop dispenser, e.g. relative to dropper part of the drop dispenser by an external force applied, for example by pressing, pushing, shifting, tilting or bending out of its original position to a displaced position without affecting the physical integrity of the container part (1B). Preferably the displacement of the displaceable section (1C) of the container part (1B) induces a deformation, preferable a reversible deformation of the container part, in which the inner volume of the container part is reduced. Optionally the container part (1B) may also comprise a stationary or substantially stationary section which is not or substantially not displaced together with the displaceable section when an external force is applied. The stationary section may or may not be present and may be a separate part connected to the displaceable section or may be a portion of the displaceable section which may not be displace relative to fixed portion of the drop dispenser.

The drop dispenser provided in step a) of the present invention also has a dropper part (1A). The "dropper part" is the portion of the drop dispenser through which the liquid composition (2) is discharged from the container part (1B) and subsequently administered. It is physically connected to the container part (1B) and connects the interior volume of the container part (1B) to the environment through an outflow channel (5) through which the liquid composition (2) to be administered is discharged. The outflow channel may optionally comprise a drop brake channel (6) which elongates the outflow channel further into the interior volume of the container part (1B).

According to step b) of the administration method of the present invention a first force is exerted to the displaceable section (1C) of the container part (1B) of the drop dispenser (1) while the drop dispenser is held in an upright position. The term "upright position" means that the drop dispenser is oriented such that the outflow channel (5) or the optional drop brake channel (6) is not in contact with the liquid composition (2) held in the container part. This is usually the case when the dropper part comprising the outflow channel is oriented upwards and the liquid composition, by the force of gravity, is held in the lowermost part, i.e. the bottom end of the drop dispenser. In this orientation, the outflow channel only contacts the gaseous phase (3) and not the liquid composition (2). Accordingly, the term "upright position" also encompasses orientations of the drop dispenser which are not completely perpendicular. It also encompasses inclined orientations of the dispenser with an inclination angle of up to 90°, often with an inclination angle of approximately 0° to 45°, more often with an inclination angle of approximately 0° to 30° between the normal axis of the drop dispenser (1) and a perpendicular reference line, as long as the liquid composition does not contact the outflow channel (5) or the optional drop brake channel (6).

Preferably, the first force is a pressuring force exerted to the displaceable section of the container part (1B), for example a pressuring force applied by the fingers of a user of the drop dispenser to a flexible wall of the container part (1B). Thereby the interior volume of the container part of the drop dispenser is reduced and the gaseous phase is at least partly or in whole, preferably partly, forced out of the drop dispenser (1) into the environment.

According to step c) of the method of the present invention the drop dispenser is then inverted to an inverted position in which the liquid composition is in contact with the outflow channel (5) or, if present, the optional drop brake channel (6). The term "inverted position" as used herein means that the drop dispenser is oriented such that the outflow channel (5) or the optional drop brake channel (6) is in contact with liquid composition (2) held in the container part. This is usually the case when the dropper part comprising the outflow channel is oriented downwards and the liquid composition, by the force of gravity, is held in the lowermost end of the drop dispenser. In this orientation, the outflow channel only contacts the liquid composition (2) and not the gaseous phase (3). Accordingly, the term "inverted position" also encompasses orientations of the drop dispenser (1) which are not completely perpendicular. It also encompasses inclined orientations of the dispenser with an inclination angle of up to 90°, often with an inclination angle of approximately 0° to 45°, more often with an inclination angle of approximately 0° to 30° between the normal axis of the drop dispenser (1) and a perpendicular reference line, as long as the liquid composition is in contact with the outflow channel (5) or the optional drop brake channel (6) of the dropper part.

According to step d) of the method of the present invention said first force exerted to the displaceable section (1C) of the container part (1B) in step b) is at least partly released while still holding the drop dispenser in the inverted position. Thereby, the inner volume of the container part (1B) is enlarged or allowed to enlarge and the pressure inside the container part (1B) is at least temporarily reduced below ambient pressure (also termed as "underpressure" in this document). This allows air from the environment to enter in the outflow channel (5) of the dropper part and prevents any liquid composition (2) from leaking unintentionally or uncontrolled from the outflow channel (5).

According to step e) of the method of the present invention a second force is exerted to the displaceable section (1C) of the container part (1B), while still holding the drop dispenser in the inverted position in which the liquid composition (2) is in contact with the outflow channel (5). In a preferred embodiment, the second force is the same kind of force as applied according to step b), preferably also a pressuring force applied by the fingers of a user of the drop dispenser to a flexible wall of the container part (1B). By exerting the second force to the displaceable part (1C) of the drop dispenser (1) the pressure inside the interior volume of the container part (1B) is raised at least temporarily above ambient pressure and the liquid composition (2) is released dropwise from the dropper part (1A) of the drop dispenser (1).

In a further embodiment, the administration method according to the present invention optionally comprises the additional step f) dropwise administering the composition to the eye, preferably to the eye lid, eye sac or an ophthalmic tissue of a subject in need thereof.

In a preferred embodiment of the present invention the drop dispenser (1) as described above is a dropper bottle (1) with a dropper part (1A) and a container part (1B), the container part (1B) comprising the displaceable section (1C).

The term "dropper bottle" (1) as used in connection with this preferred embodiment of the invention refers to a medical device that is/may be used as an eye drop delivery system (eyedropper), but which may also be helpful in administering certain compositions in a drop-by-drop manner to other parts of the body that are accessible to topical administration, such as ear, skin, nose, head, finger or other limbs. A dropper bottle may comprise a bottle part (1B) and a dropper part (1A) (see FIGS. 1-7). The bottle part (1B) is for holding the liquid ophthalmic composition to be released in a drop-by drop manner according to the present invention.

The term "bottle part" (1B) of the dropper bottle, as used herein refers to part of the dropper bottle (1) that holds the liquid (ophthalmic) composition (2) to be administered in its interior volume. Besides the liquid (ophthalmic) composition (2) the remaining part of the interior volume is filled by a gaseous phase (3). As described above, said gaseous phase (3) may comprise air or another gas, such as an inert gas (e.g. argon, nitrogen). It is understood that, as the volume of the liquid composition (2) is decreasing upon repeated use/release of drops, the volume of the gaseous phase (3) is correspondingly increasing.

The "dropper part" (1A) as used herein refers to the part of the dropper bottle (1) from which the liquid (ophthalmic) composition is physically released in a dropwise, i.e. in a drop-by-drop manner. The dropper part (1A) is or may be mounted onto the bottle part (1B), connecting the interior volume of the bottle part to the environment. This connection (fluid communication) of the interior volume to the environment is effected in sequential order (from the distal to the proximal end) by the optional drop brake channel (6) (see FIGS. 1 to 7) to the outflow channel (5) with the duct opening (4) at its distal end and the dropper mouth (7) at its proximal end. Said fluid communication allows both the liquid ophthalmic composition (2), as well as the gaseous phase (3) to be released from the dropper bottle (1) to the environment.

The term "deformable wall part (1C)" as used herein in connection with the dropper bottle of this embodiment of the invention refers to the wall part of the bottle part (1B) of the dropper bottle (1), which is fabricated in such that is allows to be deformed by a pressuring force exerted to it. The deformation of the wall part (1C) effects the interior volume to be compressed, resulting in the release of the gaseous phase (3) and/or the liquid (ophthalmic) composition (2) from the interior volume to the environment, as well as the intake of a gaseous phase (e.g. air) into the interior volume. The deformable wall part is preferably manufactured from a at least partially deformable material, preferably from an at least partially deformable plastic material, such as polypropylene or polyethylene. More preferably the deformable wall part is preferably manufactured from a at least partially manually deformable plastic material.

Preferably, the deformable wall part is manufactured from an at least partially manually deformable plastic material with a preferred thickness in the range of from 0.4 to 1.6 mm, preferably with a thickness in the range of from 0.5 to 1.0 mm, more preferably with a thickness in the range of from 0.6 to 0.8 mm.

The term "dropper brake channel" (6) of the dropper bottle according to this preferred embodiment of the invention as used herein refers to an optional channel-like device that extends from the duct opening (4) of the outflow channel (5) into the interior volume of the bottle part. When present, the dropper brake channel (6) is in fluid communication with the interior volume of the bottle part (1B) and with the outflow channel (5). The dropper brake channel may act as a means to limit or reduce the flow of the ophthalmic composition upon inversion of the dropper bottle (1).

The term "duct opening (4)" of the dropper bottle as used herein refers to the most distal end of the outflow channel (5). The duct opening (4) is preferably circular and/or has a preferred diameter in the range of from 0.15 to 1.2 mm, preferably its diameter is in the range of from 0.18 to 0.5 mm, more preferably its diameter is in the range of from 0.2 to 0.3 mm.

The term "outflow channel (5)" as used in connection with this embodiment of the invention refers to a channel-like device that connects the interior volume of the dropper bottle (1) to the environment, safeguarding the fluid (or gaseous) communication between interior volume and the environment. Herein, the outflow channel (5) is delimited at its distal end by the duct opening (4) located inside the interior volume of the dropper bottle and by the dropper mouth (7) at its very proximal end located outside the interior volume of the dropper bottle.

Upon administration, the liquid, preferably the liquid ophthalmic composition is delivered from interior volume through the outflow channel (5) to the dropper mouth (7), where the composition is released in a drop-by-drop manner. The outflow channel (5) is preferably a circular channel. Preferably, the outflow channel (5) has different diameters at its distal end (duct opening (4)) and at its proximal end (dropper mouth (7)). In one embodiment, the diameter at the distal end (duct opening (4)) is smaller than the diameter at the proximal end (dropper mouth (7)). In this embodiment, the outflow channel is narrowing from the proximal dropper mouth (7) to the distal duct opening (4). In still a further embodiment, the diameter at the distal end (duct opening (4)) is larger than the diameter at the proximal end (dropper mouth (7)).

The term "dropper mouth" (7) as used in this embodiment refers to the most proximal end of the outflow channel (5), where the drops to be released are formed. The diameter of the dropper mouth (7) is preferably circular and/or its diameter is preferably in the range of 1 to 5 mm, preferably its diameter is in the range of 2 to 3 mm, more preferably its diameter is in the range of 2.0 to 2.6 mm, even more preferably its diameter is in the range of about 2.0 to 2.4 mm.

The term "pressuring force" as used in this preferred embodiment refers to a force that is applied to the deformable wall part (1C) to effect the interior volume of the bottle part (1B) to be compressed. Preferably, said force is by manually pressuring the deformable wall part (1C), e.g. by manually squeezing.

In a further preferred embodiment, the administration method according to the present invention, the inversion of the drop dispenser (1) to the inverted position according to step (c) and the release of the first force according to step (d) is performed at least partly simultaneously. This means that the release of the first force, preferably the first pressuring force exerted to the displaceable part (1C) of the drop dispenser may or may not be performed in whole or in part during the inversion of the drop dispenser according to step c). Preferably, however, the release of the first force does not start, before the contact between the liquid composition and the outflow channel (5) is established. Irrespective of whether or not steps c) and d) are performed simultaneously in whole or in part the administration method according to the present invention it is beneficial and preferred when upon release of the first force in step d) air is at least partially sucked into the outflow channel (5) forming a barrier to prevent uncontrolled release of the liquid composition (2) from the dropper dispenser (1). Therefore, according to this beneficial embodiment of the present invention the reduced pressure generated inside the interior volume of the container part (1B) prevents the unintended, in many cases non-dropwise and therefore non-reproducible release of the liquid composition (2) from the drop dispenser (1).

In a further embodiment of the first aspect of the invention, the method optionally further comprises the steps:

g) releasing the second pressuring force from the displaceable part (1C) of the container or bottle part (1B), while still holding the drop dispenser or dropper bottle respectively in the inverted position, thereby stopping the release of the liquid composition (2), and h) optionally exerting one or more further pressuring force(s) to the displaceable or deformable wall part (1C) of the container or bottle part (1B), while still holding the drop dispenser or dropper bottle in an inverted position, thereby releasing further liquid composition (2) in a dropwise manner from the dropper part (1A) and subsequently releasing the one or more further pressuring force(s) from the displaceable part (1C) of the container or bottle part (1B).

The liquid composition utilized in the method of the present invention may be a water-containing or alternatively a water-free composition. Examples of composition successfully utilized in practicing the method of the present invention are listed in Table 2.

In a further preferred embodiment of the present invention the liquid composition (2) to be administered in a dropwise fashion is an ophthalmic composition, whereas the term "ophthalmic" as used herein means that the liquid composition can be topically administered to the eye, to the eye surface or to an eye tissue of a human or an animal.

The liquid composition may comprise water, dissolved salts, buffer solutions and solvents known to those of skill in the art to be compatible with the above-described ophthalmic administration.

Accordingly, a broad diversity of commercially available, water-based ophthalmic compositions, such as e.g. Systane®, Arteleac®, Refresh (see Table 2) and the like are suited as liquid compositions (2) to be administered according to the method of the present invention.

Further, the liquid composition (2) may comprise one or more excipients, such as an organic cosolvent, such as an oil selected from glyceride oils, liquid waxes, and liquid paraffin or mineral oil, or said liquid composition may comprise an organic solvent exhibiting a high degree of biocompatibility, such as glycerol, propylene glycol, polyethylene glycol or ethanol.

The liquid composition (2) to be administered may be used in form of a solution or a suspension or an emulsion. Further, it may generally be used at different temperatures, such as different room or ambient temperatures. Furthermore, it may be used in a cooled state, for example after storage in a cooler or freezer. Typically, the liquid composition (2) to be administered may be used at a temperature (of the liquid, not necessarily of the surroundings) of approximately from −15 to 40° C., more typically of from −10° C. to 37° C. In a preferred embodiment of the present invention the liquid composition has a temperature in the range from −7° C. to 30° C., preferably in the range from 20° C. to 30° C.

The liquid composition (2) optionally comprises one or more pharmaceutical active ingredients (APIs) such as for example: prostaglandin analogs (e.g. latanoprost, unoprostone, travoprost, bimatoprost, tafluprost), g-blockers, (e.g. timolol, brimonidine), cabonic anhydrase inhibitors (e.g. acetazolamide, dorzolamide, methazolamide, brinzolamide), antihistamines (e.g. olopatadine, levocabastine), corticosteroids (e.g. loteprednol, prednisolone, dexamethasone), fluorquinolone antibiotics (e.g. moxifloxacin, gatifloxacin, ofloxacin, levofloxacin), aminoglycoside antibiotics (e.g. tobramycin), macrolide antibiotics (e.g. azithromycin), VEGF-inhibitors (e.g. ranibizumab, bevacizumab, aflibercept), macrolide immunsuppressants (e.g. cyclosporine, tacrolimus, sirolimus), NSAIDs (e.g. bromfenac, nepafenac, diclofenac, ketorolac).

In a preferred embodiment, the liquid composition (2) to be topically administered according to present invention comprises a liquid semifluorinated alkane or a mixture of two or more different semifluorinated alkanes.

The term "semifluorinated alkane" (also referred to as "SFA" throughout this document) refers to a linear or branched compound composed of at least one perfluorinated segment (F-segment) and at least one non-fluorinated hydrocarbon segment (H-segment). More preferably, the semifluorinated alkane is a linear or branched compound composed of one perfluorinated segment (F-segment) and one non-fluorinated hydrocarbon segment (H-segment). Preferably, said semifluorinated alkane is a compound that exists in a liquid state at least at one temperature within the temperature range of 4° to 40° C., with the perfluorinated segment and/or the hydrocarbon segment of the said SFA optionally comprising or consisting of a cyclic hydrocarbon segment, or optionally said SFA within the hydrocarbon segment comprising an unsaturated moiety.

Preferably, the F-segment of a linear or branched SFA comprises between 3 to 10 carbon atoms. It is also preferred that the H-segment comprises between 3 to 10 carbon atoms. It is particularly preferred that the F- and the H-segment comprise, but independently from one another, 3 to 10 carbon atoms. Preferably, each segment independently from another is having carbon atoms selected from the range of 3 to 10.

It is further preferred, that the F-segment of a linear or branched SFA comprises between 4 to 10 carbon atoms and/or that the H-segment comprises between 4 to 10 carbon atoms. It is particularly further preferred that the F- and the H-segment comprise, but independently from one another, 4 to 10 carbon atoms. Preferably, each segment is independently from another having carbon atoms selected from the range of 4 to 10.

Optionally, the linear or branched SFA may comprise a branched non-fluorinated hydrocarbon segment comprising one or more alkyl groups selected from the group consisting of —$CH_3$, $C_2H_5$, $C_3H_7$ and $C_4H_9$ and/or the linear or branched SFA may comprise a branched perfluorinated hydrocarbon segment, comprising one or more perfluorinated alkyl groups selected from the group consisting of —$CF_3$, $C_2F_5$, $C_3F_7$ and $C_4F_9$.

It is further preferred that the ratio of the carbon atoms of the F-segment and the H-segment (said ratio obtained by dividing the number of carbon atoms in the F-segment by the numbers of carbon atoms in the H-segment; e.g. said ratio is 0.75 for 1-perfluorohexyloctane (F6H8)) of a linear or branched SFA is 0.5, more preferably said ratio is 0.6. It is further preferred that the ratio of the carbon atoms of the F-segment and the H-segment is in the range between 0.6 and 3.0, more preferably said ratio is between 0.6 and 1.0.

In a preferred embodiment of the present invention the semifluorinated alkane refers to a linear compound composed of at least one perfluorinated segment (F-segment) and at least one hydrocarbon segment (H-segment). More preferably, said semifluorinated alkane is a linear compound composed of one perfluorinated segment (F-segment) and one hydrocarbon segment (H-segment).

According to another nomenclature, the linear semifluorinated alkanes may be referred to as FnHm, wherein F means the perfluorinated hydrocarbon segment, H means the non-fluorinated hydrocarbon segment and n, m is the number of carbon atoms of the respective segment. For example, F4H5 is used for 1-perfluorobutylpentane.

Preferably, the F-segment of a linear SFA comprises between 3 to 10 carbon atoms. It is also preferred that the H-segment comprises between 3 to 10 carbon atoms. It is particularly preferred that the F- and the H-segment comprise, but independently from one another, 3 to 10 carbon atoms. Preferably, each segment independently from another is having carbon atoms selected from the range of 3 to 10.

It is further preferred, that the F-segment of a linear SFA comprises between 4 to 10 carbon atoms and/or that the H-segment comprises between 4 to 10 carbon atoms. It is particularly further preferred that the F- and the H-segment comprise, but independently from one another, 4 to 10 carbon atoms. Preferably, each segment is independently from another having carbon atoms selected from the range of 4 to 10.

Optionally, the linear SFA may comprise a branched non-fluorinated hydrocarbon segment comprising one or more alkyl groups selected from the group consisting of —$CH_3$, $C_2H_5$, $C_3H_7$ and $C_4H_9$ and/or the linear SFA may comprise a branched perfluorinated hydrocarbon segment, comprising one or more perfluorinated alkyl groups selected from the group consisting of —$CF_3$, $C_2F_5$, $C_3F_7$ and $C_4F_9$. It is further preferred that the ratio of the carbon atoms of the F-segment and the H-segment (said ratio obtained by dividing the number of carbon atoms in the F-segment by the numbers of carbon atoms in the H-segment; e.g. said ratio is 0.75 for 1-perfluorohexyloctane ($F_6H_8$)) of a linear SFA is 0.5, more preferably said ratio is ≥0.6. It is further preferred that the ratio of the carbon atoms of the F-segment and the H-segment is in the range from 0.6 to 3.0, more preferably said ratio is in the range from 0.6 to 1.0.

Preferably, the semifluorinated alkane is a linear compound of the formula $F(CF_2)_n(CH_2)_mH$ wherein n and m are integers independently selected from the range of 3 to 10, more preferably the semifluorinated alkane is a linear compound of the formula $F(CF_2)_n(CH_2)_mH$ wherein n and m are integers independently selected from the range of 4 to 10. Even more preferred the semifluorinated alkane is a liquid of the formula $F(CF_2)_n(CH_2)_mH$ wherein n and m are integers independently selected from the range of 4 to 10.

Preferably, the linear SFA is selected from the group consisting of F4H4, F4H5, F4H6, F4H7, F4H8, F5H4, F5H5, F5H6, F5H7, F5H8, F6H2, F6H4, F6H6, F6H7, F6H8, F6H9, F6H10, F6H12, F8H8, F8H10, F8H12, F10H10, more preferably said linear SFA is selected from the group consisting of F4H4, F4H5, F4H6, F5H4, F5H5, F5H6, F5H7, F5H8, F6H2, F6H4, F6H6, F6H7, F6H8, F6H9, F6H10, F8H8, F8H10, F8H12, F10H10, even more preferably the linear SFA is selected from the group consisting of F4H4, F4H5, F4H6, F5H4, F5H5, F5H6, F5H7, F5H8, F6H4, F6H6, F6H7, F6H8, F6H9, F6H10, F8H8, F8H10, F8H12, F10H10, most preferably the linear SFA is selected from the group consisting of F4H4, F4H5, F4H6, F5H5, F5H6, F5H7, F5H8, F6H6, F6H7, F6H8, F6H9, F6H10, F8H8, F8H10, F8H12, F10H10. In a further preferred embodiment, the linear SFA is selected from the group consisting of F4H5, F4H6, F5H6, F5H7, F6H6, F6H7, F6H8. In an even further preferred embodiment the linear SFA is selected from F4H5 and F6H8.

The liquid composition (2) to be administered by the method of the present invention may optionally comprise water. In a preferred embodiment, however, the liquid composition is water-free or at least substantially water-free. When comprising water the liquid composition may be a aqueous composition, typically comprising water up to approximately 99% by weight of the final composition or alternatively the liquid composition may be an emulsion, typically comprising up to approximately 90% by weight of the final composition, more typically approximately 0.01 to 80%, even more typically approximately 0.01 to 50%.

The liquid composition (2), preferably the substantially water-free solution comprising a liquid semifluorinated alkane or a mixture of two or more different semifluorinated alkanes to be administered usually has a density measured at 25° C. in the range of 0.7 to 1.9 g/cm$^3$, preferably in the range of 1.0 and 1.7 g/cm$^3$, more preferably in the range of 1.2 to 1.4 g/cm$^3$. The viscosity of the liquid composition (2) measured at 25° C. versus air usually may be in the range of 0.3 to 5.2 mPa s, preferably in the range of 0.9 to 4.0 mPa s, more preferably in the range of 1.0 to 3.5 mPa s.

The surface tension of the liquid composition (2) versus air measured at 25° C. usually is in the range of 15 to 75 mN/m, preferably in the range of 15 to 30 mN/m, more preferably in the range of 15 to 23 mN/m.

Further, the composition utilized in the method of the present invention may comprise one or more active pharmaceutical ingredient (APIs) or alternatively may not comprise does or does not comprise an active pharmaceutical ingredient. Examples of liquid ophthalmic compositions are listed in Table 2.

According to the present invention a broad range of dropper configurations can be utilized when practicing the administration method according to the present invention (underpressure method). Examples of such droppers are listed in Table 1, with its dropper bottle configurations listed in Table 2. The dropper bottle (1) may comprise configurations of the dropper part (1A) and the bottle part (1B) as defined above.

In still a further embodiment of the first aspect of the invention, the administration method optionally further comprises the steps:
i) inverting the drop dispenser or dropper bottle (1) as to return to an upright position, thereby sucking air from environment through the outflow channel (5) into the interior volume, as to effect underpressure relief in the dropper bottle (1);
j) closing and storing the drop dispenser or dropper bottle (1);
k) optionally repeating steps a) to j).

In a second aspect, the invention relates to the use of the method according to the first aspect of the invention for preventing or treating an ocular disease or any symptoms or conditions associated therewith.

The term "ocular disease" as used herein refers to a disease or a disorder of the eye, including disorders or diseases of the eyelid, lacrimal system, orbit, conjunctiva, sclera, cornea, iris, ciliary body, lens, choroid or retina, including disorders classified by WHO according to ICD codes H00-H06, H10-H13, H15-H22, H25-H28, H30-H36, H40-H42, H43-H45, H46-H48, H49-H52, H53-H54, H55-H59.

Generally, the administration of the ophthalmic composition (2) according to the method of the present invention may be carried out regularly, such as up to once per week, or up to once per day or up to 8, 7, 6, 5, 4, 3 or up to 2 times per day.

In a third aspect, the invention relates to a method of treating an ocular disease or any symptoms or conditions associated therewith comprising dropwise administration a liquid ophthalmic composition according to the method of the first aspect of the present invention.

In a fourth aspect, the present invention relates to a drop dispenser (1), comprising
a container part (1B) with an interior volume partially filled with the liquid composition (2) and a gaseous phase (3) filling the remainder of the interior volume at ambient pressure, the container part (1B) having a displaceable section (1C) and optionally a substantially stationary section, and
a dropper part (1A) in physical connection and in fluid communication with the interior volume of the container part (1B), comprising an outflow channel (5), connecting the interior volume of the container part (1B) to the environment; wherein at least a portion of the outflow channel (5) has an inner diameter in the range of 0.09 to 0.19 mm.

The drop dispenser (1) according to this aspect of the invention is particularly suitable and can preferably be adapted to be used in the administration method according to the first aspect of the invention. However, it should be understood the drop dispenser according to this aspect of the invention can also be used independently of the administration method according to the first aspect of the invention. Accordingly, as the drop dispenser provided in step a) of the present invention, it comprises a container part (1B) and a dropper part (1A) which are as described in connection with the first aspect of the invention.

The container part (1B) preferably also has a displaceable section (1C) and also holds a gaseous phase (3) which fills the remainder of the interior volume which is not filled with the liquid composition (2), whereas the terms displaceable section (1C), gaseous phase and liquid composition are also as defined in connection with the drop dispenser provided in the first aspect of the invention.

Furthermore, the drop dispenser of the present aspect of the invention has a dropper part (1A) as the one provided for in step a) of the present administration method. The "dropper part" is the portion of the drop dispenser through which the liquid composition (2) is discharged from the container part (1B) and subsequently administered. It is physically connected to the container part (1B) and connects the interior volume of the container part (1B) to the environment through an outflow channel (5) through which the liquid composition (2) to be administered is discharged. In this embodiment also, the outflow channel may optionally comprise a drop brake channel (6) which elongates the outflow channel further into the interior volume of the container part (1B).

The term "outflow channel (5)" as used in connection with this embodiment of the invention refers to a channel-like device that connects the interior volume of the dropper bottle (1) to the environment, safeguarding the fluid (or gaseous) communication between interior volume and the environment. Herein, the outflow channel (5) is delimited at its distal end by the duct opening (4) located inside the interior volume of the dropper bottle and by the dropper mouth (7) at its very proximal end located outside the interior volume of the dropper bottle. Upon administration, the liquid, preferably the liquid ophthalmic composition is delivered from interior volume through the outflow channel (5) to the dropper mouth (7), where the composition is released in a drop-by-drop manner.

The drop dispenser according to this aspect of the invention is characterized in that at least a portion of the outflow channel (5) has an inner diameter in the range of 0.09 to 0.19 mm, preferably in the range of from about 0.10 to about 0.18 mm, more preferably from about 0.11 to about 0.17 mm, even more preferably from about 0.12 to about 0.16 mm, yet more preferably from about 0.13 to about 0.16 mm or even from about 0.14 to about 0.16 mm and most preferably of about 0.15 mm. The term "at least a portion of" the outflow channel means that either the whole channel over its entire length has an inner diameter in the described range or that only a portion, part or fraction of the outflow channel has an inner diameter in the defined range or ranges. For example, about 75% or less, 60% or less, 50% or less or even 40%, 30% or even only 25% or less of the total length of the outflow channel (5) may have an inner diameter in the range as defined above. In other embodiments, only a small portion, such as only 20% or less or even only 10% or less of the total length of the outflow channel may have an inner diameter in the range as defined above.

In a preferred embodiment, the duct opening (4) of the outflow channel has an inner diameter in the range of 0.09 to 0.19 mm, preferably in the range of from about 0.10 to about 0.18 mm, more preferably from about 0.11 to about 0.17 mm, even more preferably from about 0.12 to about 0.16 mm, yet more preferably from about 0.13 to about 0.16 mm or even from about 0.14 to about 0.16 mm and most preferably of about 0.15 mm. In yet further embodiments, the duct opening (4) and a portion of the outflow channel (5) beginning at the duct opening have an inner diameter in the range of 0.09 to 0.19 mm.

In this aspect of the invention also, the outflow channel (5) may have different cross-sectional shapes, such as circular, elliptic, rectangular or quadratic or the like, however, it is preferably a circular channel. In cases in which the duct channel does not have a circular cross-sectional shape the term "inner diameter" is to be understood as the largest diameter of such particular shape. Preferably, the outflow channel (5) has different diameters at its distal end (duct opening (4)) and at its proximal end (dropper mouth (7)). In one embodiment, the diameter at the distal end (duct opening (4)) is smaller than the diameter at the proximal end (dropper mouth (7)). In this embodiment, the outflow channel is narrowing from the proximal dropper mouth (7) to the distal duct opening (4). In still a further embodiment, the diameter at the distal end (duct opening (4)) is larger than the diameter at the proximal end (dropper mouth (7)).

The term "duct opening (4)" of the dropper bottle as used herein refers to the most distal end of the outflow channel (5). Accordingly, the duct opening (4) is preferably circular and/or has a preferred diameter which may also be in the range of from 0.09 to 0.19 mm or, in cases in which the portion of the outflow channel (5) having an inner diameter of 0.09 to 0.19 mm does not comprise the duct opening (4), preferably the inner diameter of the duct opening (4) is in the range of from 0.2 to 0.5 mm, more preferably its diameter is in the range of from 0.2 to 0.3 mm.

The term "dropper mouth" (7) as used in this embodiment refers to the most proximal end of the outflow channel (5), where the drops to be released are formed. The diameter of the dropper mouth (7) is preferably circular and/or its diameter is preferably in the range of 1 to 5 mm, preferably its diameter is in the range of 2 to 3 mm, more preferably its diameter is in the range of 2.0 to 2.6 mm, even more preferably its diameter is in the range of about 2.0 to 2.4 mm.

In a particularly preferred embodiment, the duct opening (4) of the outflow channel has an inner diameter of about 0.15 mm and the diameter of the dropper mouth (7) is about 2.0 to 2.4 mm, preferably about 2.4 mm. In yet a further particularly preferred embodiment the duct opening (4) of the outflow channel has an inner diameter of about 0.15 mm and the inner diameter of the rest of the outflow channel including the dropper mouth (7) is about 2.0 to 2.4 mm, preferably about 2.4 mm. In both embodiments, the duct opening (4), the outflow channel (5) and/or the dropper mouth (7) preferably has a circular cross-sectional shape.

According to this aspect of the invention also, it is to be understood that the optional drop brake channel (6), if present, does not form part of the outflow channel (5) which extends from the duct opening (4) and therefore does not contribute to the total length of the outflow channel (5).

One advantage of the reduced diameter of at least a portion of the outflow channel of the drop dispenser according to the present aspect of the invention is that the undesired spontaneous outflow or drop-formation of the liquid composition, preferably the liquid ophthalmic composition can be reduced significantly for aqueous as well as non-aqueous compositions. Especially in cases of non-aqueous compositions, especially for SFA-containing compositions this has been found to be particularly beneficial.

It has been found that for practical purposes a range of 0.09 to 0.19 mm of at least a portion of the outflow channel is preferable as it combines significantly reduced spontaneous outflow with acceptable forces necessary to press the liquid composition through the outflow channel (5). Particularly in view of a possible use of the disclosed drop dispenser (1) characterized by least a portion of the outflow channel (5) having an inner diameter in the range of 0.09 to 0.19 mm in an administration method according to the first aspect of the invention this has been shown of considerable importance for e.g. elderly or disabled users.

Furthermore, it has been found that the drop dispenser according to the present aspect of the invention offers higher precision and reproducibility of the drop sizes and volumes to be dispensed, independent of the temperature of the drop dispenser, liquid composition and/or the environment as well as the actual filling level of the drop dispenser or "headspace" above the liquid composition in the drop dispenser.

The outflow channel (5) with at least a portion having an inner diameter in the range of 0.09 to 0.19 mm according to this aspect of the invention can be produced by standard techniques, such as laser drilling or welding.

In a fifth aspect, the present invention relates to a kit comprising
    a drop dispenser (1) at least partially filled with a liquid composition (2) and a gaseous phase (3) for the use in a method according to the first aspect of the invention and
    directions for use of the drop dispenser (1) in a method according to the first aspect of the invention.

The directions or instructions for use comprised by the kit according to this aspect of the invention may be in in any form suited to instruct the user how to perform the topical administration method according to first aspect of the invention (underpressure method). It may be in any readable or tangible form, preferably in printed form or in any machine- or computer-readable form preferably in form of a machine-readable optical label such as, for example, a barcode or a QR-code. In a particularly preferred embodiment the directions for use are provided in form of an instruction leaflet, product or package insert or as an enclosed label. Preferably the directions or instructions for use are provided in printed form, for example in form of a printed label, which may be provided together with the drop dispenser (1) or dropper bottle (1) to be used according to the method of the first aspect of the invention. For example, such a label may be packaged together with the said drop dispenser (1) or dropper bottle (1).

In summary, the present invention comprises the following numbered items:

1. A method for dropwise topical administration of a liquid composition (2), comprising the steps of:
   a) providing a drop dispenser (1), comprising
      a container part (1B) with an interior volume partially filled with the liquid composition (2) and a gaseous phase (3) filling the remainder of the interior volume at ambient pressure, the container part (1B) having a displaceable section (1C) and optionally a substantially stationary section, and
      a dropper part (1A) in physical connection and in fluid communication with the interior volume of the container part (1B), comprising an outflow channel (5), connecting the interior volume of the container part (1B) to the environment;
   b) exerting a first force to the displaceable section (1C) of the container part (1B) of the drop dispenser (1) while holding the drop dispenser (1) in an upright position in which the outflow channel (5) is not in contact with the liquid composition (2), thereby reducing the interior volume of the container part (1B) and forcing the gaseous phase (3) of the interior volume at least partially out of the drop dispenser (1) into the environment;
   c) inverting the drop dispenser (1) to an inverted position in which the liquid composition (2) is in contact with the outflow channel (5);
   d) releasing said first force from the displaceable section (1C) of the container part (1B) at least partly, thereby reducing the pressure inside the container part (1B) below ambient pressure; and
   e) exerting a second force to the displaceable section (1C) of the container part (1B), while still holding the drop dispenser in the inverted position in which the liquid composition (2) is in contact with the outflow channel (5), thereby raising the pressure inside the interior volume of the container part (1B) above ambient pressure and releasing the liquid composition (2) dropwise from the dropper part (1A) of the drop dispenser (1).

2. The method according to item 1, wherein the inversion of the drop dispenser (1) to the inverted position according to step (c) and the release of the first force according to step (d) is performed at least partly simultaneously.

3. The method according to any of the preceding items, wherein the liquid composition comprises a liquid semi-fluorinated alkane.

4. The method according to any of the preceding items, wherein the liquid composition is a water-containing or a water-free composition.

5. The method according to any of the preceding items, wherein the outflow channel is narrowing from the proximal dropper mouth (7) to the distal duct opening (4).

6. The method according to an of the preceding items, wherein the drops to be released are formed at the dropper mouth (7) at the proximal end of the outflow channel (5).

7. The method according to any of the preceding items, wherein the exerting a pressuring force is by manually compressing (squeezing) the displaceable part or deformable wall part (1C).

8. The method according to any of the preceding items, wherein the drop dispenser or dropper bottle in step (e) is tilted in the inverted position during the dropwise release of the composition, preferably the drop dispenser or dropper bottle is tilted up to 90° in the inverted position, more preferably the drop dispenser or dropper bottle is tilted up to 45° in the inverted position, wherein the angle is measured between the normal axis of the drop dispenser or dropper bottle and a perpendicular reference line.

9. The method according to any of the preceding items, wherein air is sucked in from the environment through the outflow channel (5) into the interior volume of the container or bottle part (1B), when said first pressuring force is released.

10. The method according to any of the preceding items, wherein the underpressure in the interior volume of the dropper bottle (1) prevents unintentional and/or uncontrolled release of liquid composition (2) from the dropper mouth (7) through the outflow channel (5).

11. The method according to any of the preceding items, wherein the dropper part (1A) comprises a drop brake channel (6), preferably with a circular cross section, extending the outflow-channel (5) from the duct opening (4) into the interior volume of the container or bottle part (1B).

12. The method according to any of the preceding items, wherein the duct opening (4) is preferably circular and/or has a preferred diameter in the range of from 0.15 to 1.2 mm, more preferably in the range of from 0.18 to 0.5 mm, and even more preferably in the range of from 0.2 to 0.3 mm.

13. The method according to any of the preceding items, wherein the diameter of the dropper mouth (7) is between 1 and 5 mm, preferably its diameter is between 2 and 3 mm, more preferably its diameter is between 2.0 and 2.6 mm, even more preferably its diameter is about 2.0 to 2.4 mm.

14. The method according to any of the preceding items, wherein the diameter of the dropper brake channel (6) is larger than the diameter of the duct opening (4).

15. The method according to any of the preceding items, wherein the dropper part (1A) and the container part or bottle part (1B) are manufactured from plastic material, preferably from polypropylene or polyethylene.

16. The method according to any of the preceding items, wherein the bottle part (1B) is manufactured with the deformable wall part (1C) being manually deformable, preferably the deformable wall part (1C) having a wall thickness of between 0.4 and 1.6 mm, preferably having a wall thickness of between 0.5 and 1.0 mm, more preferably having a wall thickness of between 0.6 and 0.8 mm.

17. The method according to any of the preceding items, wherein the gaseous phase (3) comprises air and/or an inert gas, such as nitrogen or argon.

18. The method according to any of the preceding items, wherein the liquid composition (2) is characterized by a density measured at 25° C. in the range of 0.7 to 1.9 g/cm$^3$, preferably in the range of 1.0 and 1.7 g/cm$^3$, more preferably in the range of 1.2 to 1.4 g/cm$^3$.

19. The method according to any of the preceding items, wherein the composition is characterized by a viscosity measured at 25° C. versus air in the range be in the range of 0.3 to 5.2 mPa s, preferably in the range of 0.9 to 4.0 mPa s, more preferably in the range of 1.0 to 3.5 mPa s.

20. The method according to any of the preceding items, wherein the composition is characterized by a surface tension versus air measured at 25° C. is in the range of 15 to 75 mN/m, preferably in the range of 15 to 30 mN/m, more preferably in the range of 15 to 23 mN/m.

21. The method according to any of the preceding items, wherein the liquid composition (2) comprises a liquid linear or branched semifluorinated alkane composed of one perfluorinated segment and one non-fluorinated hydrocarbon segment, preferably each segment independently having carbon atoms selected from the range of 4 to 10.

22. The method according to any of the preceding items, wherein the semifluorinated alkane is a liquid of the formula $F(CF_2)_n(CH_2)_mH$ wherein n and m are integers independently selected from the range of 4 to 10.

23. The method according any of the preceding items, wherein the semifluorinated alkane is a liquid selected from the group consisting of F4H4, F4H5, F4H6, F4H7, F4H8, F5H4, F5H5, F5H6, F5H7, F5H8, F6H2, F6H4, F6H6, F6H7, F6H8, F6H9, F6H10, F6H12, F8H8, F8H10, F8H12, F10H10, more preferably said linear SFA is selected from the group consisting of F4H5, F4H6, F5H6, F5H7, F6H6, F6H7, F6H8 most preferably the semifluorinated alkane is selected from F4H5 and F6H8.

24. The method according to any of the preceding items, wherein the composition is in form of a solution or a suspension or in form of an emulsion.

25. The method according to any of the preceding items, wherein the liquid composition does or does not comprise a pharmaceutical active ingredient.

26. The method according to any of the preceding items, wherein the composition further comprises one or more excipients.

27. The method according to any of the preceding items, further comprising the step: f) dropwise administering the composition to the eye, preferably to the eye lid, eye sac or an ophthalmic tissue of a subject in need thereof.

28. The method according to item 27, wherein the administering of the ophthalmic composition (2) is carried out up to once per week, or up to once per day or up to 8, 7, 6, 5, 4, 3 or up to 2 times per day.

29. The method according to any of the preceding items, further comprising the steps:
g) releasing the second pressuring force from the displaceable part (1C) of the container or bottle part (1B), while still holding the drop dispenser or dropper bottle respectively in the inverted position, thereby stopping the release of the liquid composition (2), and
h) optionally exerting one or more further pressuring force(s) to the displaceable or deformable wall part (1C) of the container or bottle part (1B), while still holding the drop dispenser or dropper bottle in an inverted position, thereby releasing further liquid composition (2) in a dropwise manner from the dropper part (1A) and subsequently releasing the one or more further pressuring force(s) from the displaceable part (1C) of the container or bottle part (1B).

30. The method according to item 29, further comprising the steps:
i) inverting the drop dispenser or dropper bottle (1) as to return to an upright position, thereby sucking air from environment through the outflow channel (5) into the interior volume, as to effect underpressure relief in the dropper bottle (1);
j) closing and storing the drop dispenser or dropper bottle (1);
k) optionally repeating steps a) to j).

31. The method according to any of the preceding items, wherein the drop dispenser (1), comprises
a container part (1B) with an interior volume partially filled with the liquid composition (2) and a gaseous phase (3) filling the remainder of the interior volume at ambient pressure, the container part (1B) having a displaceable section (1C) and optionally a substantially stationary section, and
a dropper part (1A) in physical connection and in fluid communication with the interior volume of the container part (1B), comprising an outflow channel (5), connecting the interior volume of the container part (1B) to the environment; wherein at least a portion of the outflow channel (5) has an inner diameter in the range of 0.09 to 0.19 mm.

32. Use of a method according to any of the preceding items for preventing or treating an ocular disease or any symptoms or conditions associated therewith.

33. Method of treating an ocular disease or disorder or any symptoms or conditions associated therewith, comprising dropwise administration of a liquid ophthalmic composition according to the method of any of the preceding items.

34. A drop dispenser (1), comprising
a container part (1B) with an interior volume partially filled with the liquid composition (2) and a gaseous phase (3) filling the remainder of the interior volume at ambient pressure, the container part (1B) having a displaceable section (1C) and optionally a substantially stationary section, and
a dropper part (1A) in physical connection and in fluid communication with the interior volume of the container part (1B), comprising an outflow channel (5), connecting the interior volume of the container part (1B) to the environment; wherein at least a portion of the outflow channel (5) has an inner diameter in the range of 0.09 to 0.19 mm.

35. A kit comprising
a drop dispenser (1) at least partially filled with a liquid composition (2) and a gaseous phase (3) for the use in a method according to the method of any of items 1 to 30 and
directions for use of the drop dispenser (1) in a method according to the method of any of items 1 to 30.

36. The kit according to item 34, wherein the directions for use are provided in form of an instruction leaflet, product or package insert or as an enclosed label.

DESCRIPTION OF THE DRAWINGS

List of Reference Numerals 1 drop dispenser or dropper bottle
1A dropper part of the drop dispenser or dropper bottle
1B container part of the drop dispenser or bottle part of the dropper bottle
1C displaceable section of the container part or dropper bottle
2 liquid composition
3 gaseous phase
4 duct opening of the outflow channel
5 outflow channel
6 drop brake channel
7 dropper mouth of the outflow channel FIG. 1(A) shows a schematic representation of a drop dispenser (1) or a dropper bottle (1) in the upright position with the dropper mouth (7) facing upwards. The drop dispenser or dropper bottle (1) comprises a container or bottle part (1B) and a dropper part (1A). The container part or bottle part (1B) comprises an interior volume that is at least partially filled with the liquid ophthalmic composition (2). The remainder of the interior volume of the container or bottle part (1B) is filled with a gaseous phase (3). The wall of the container or bottle part has a displaceable section (1C) to allow a pressuring force to compress the interior volume (e.g. by manual squeezing). The dropper part (1A) is mounted onto the container or bottle part (1B), connecting the interior volume of the bottle part (1B) via the optional drop brake channel (6) and via the outflow channel (5) with the environment. Herein, the fluid communication of the interior volume of the container or bottle part (1B) to the environment is effected in sequential order (from distal to proximal end) by the optional drop brake channel (6) and the outflow channel (5). The outflow channel (5) is delimited by the duct opening (4) at the distal end and by the dropper mouth (7) at the proximal end. In this upright position the liquid composition (2) does not contact the neither the outflow channel (5) nor the optional drop brake channel (6).

FIG. 1(B) is a schematic representation of the dropper part (1A) of the drop dispenser or dropper bottle (1), showing the diameter positions of the optional dropper brake channel (6), of the duct opening (4) and of the dropper mouth (7).

FIG. 2(A) shows a schematic representation of a slightly different configuration of the drop dispenser or dropper bottle (1) in the upright position (with the dropper mouth (7) facing upwards) comprising a bottle or container part (1B) and a dropper part (1A). The bottle part (1B) comprises an interior volume that is at least partially filled with the liquid ophthalmic composition (2) and the remainder of the interior volume of the bottle part (1B) is filled with a gaseous phase (3). The wall of the bottle part (1C) is deformable as to allow a pressuring force to compress the interior volume (e.g. by manual squeezing). The dropper part (1A) is mounted onto the bottle part (1B), connecting the interior volume of the bottle part (1B) via the optional drop brake channel (6) and, via the outflow channel, (5) with the environment. Herein, the fluid communication of the interior volume of the bottle part (1B) to the environment is effected in sequential order (from distal to proximal end) by the optional drop brake channel (6) and the outflow channel (5). The outflow channel (5) is delimited by the duct opening (4) at the distal end and by the dropper mouth (7) at the proximal end. In contrast to the schematic representation of FIG. 1 the diameter of the outflow channel (5) is not increasing continuously in direction from the duct opening (4) to the dropper mouth (7) of the outflow channel.

FIG. 2(B) shows an enlarged schematic representation of the modified dropper part (1A) according to FIG. 2(A), showing the diameter positions of the optional dropper brake channel (6), of the duct opening (4) and of the dropper mouth (7).

FIG. 3(A) shows a schematic representation of the drop dispenser or dropper bottle (1) in the inverted position (with the dropper mouth (7) facing downwards) when a conventional method (e.g. pressure method or inversion method) known from administration of water-based ophthalmic compositions is applied for the administration of an ophthalmic compositions comprising a SFAs: As can be seen the outflow channel (5) is filled with the SFA-comprising ophthalmic composition and the liquid composition (2) is unintentionally (uncontrolled) released from the dropper mouth (7) in a dropwise or non-dropwise fashion. This usually is the case when applying the known pressure method or the known inversion method without exerting a pressuring force to the deformable wall part of the dropper bottle (1C) while the dropper bottle (1) is (still) in the upright position.

FIG. 3(B) shows a schematic representation of the dropper bottle (1) in the inverted position when the method according to the first aspect of the present invention (underpressure method) is applied for administration of an ophthalmic composition comprising SFAs: Thereby, the underpressure in the interior volume of the dropper bottle (1) prevents uncontrolled and unintentional release of liquid composition (2) from the dropper mouth (7) through the outflow channel (5). Only when a second pressuring force is exerted to the deformable wall part (1C) of the dropper bottle drops of the liquid composition (2) comprising an SFA are released in controlled manner from the drop dispenser (1). According to the present invention, the underpressure generated in the interior volume (mainly in the gaseous phase (3) of the bottle part (1B) warrants that uncontrolled (unintentional) release of drops of compositions comprising SFAs is prevented effectively.

Figure 4:
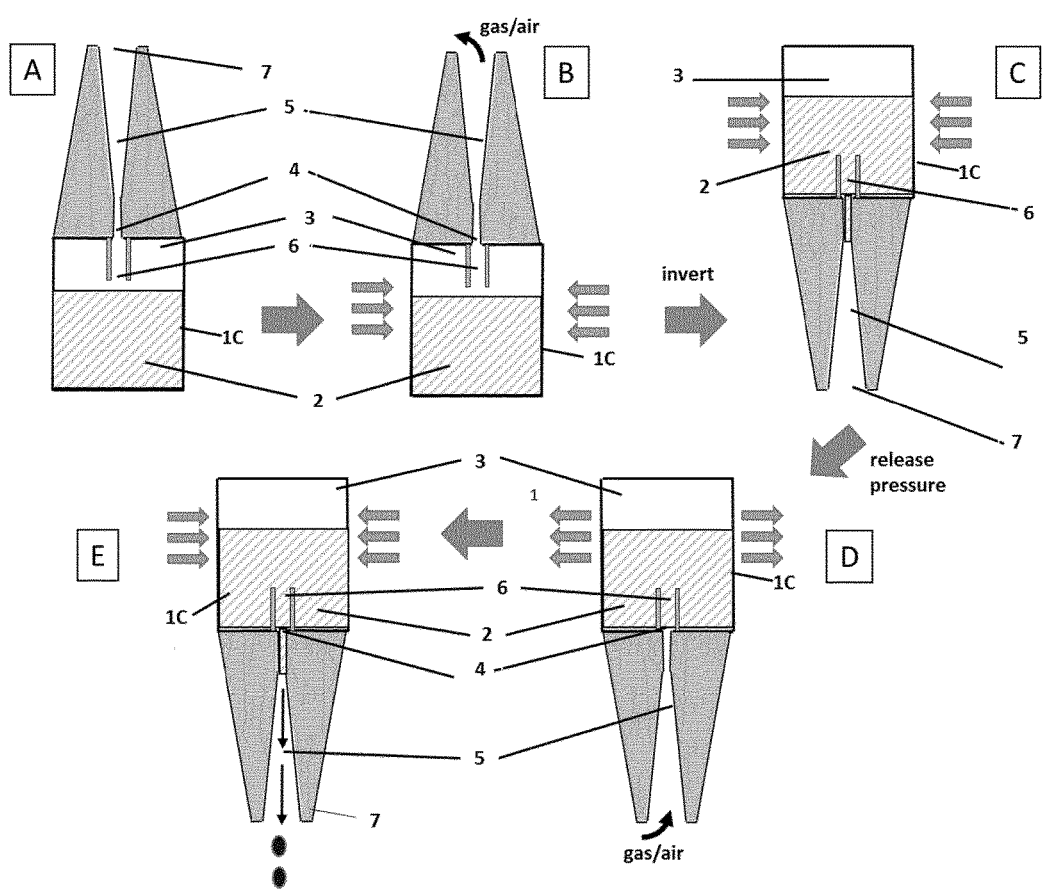
FIG. 4: Schematic representation of the administration method of the present invention (underpressure method)

FIG. 4 is a schematic representation of the administration method of the present invention (underpressure method) comprising sequentially the steps a) to e) as described above:

FIG. 4(A) schematically shows the starting position with the dropper bottle (1) in the upright position, with no underpressure present in the interior volume of the bottle part (1B), the dropper mouth (7) pointing upwards.

In FIG. 4(B) a first pressurizing force is exerted to the deformable wall part of the bottle (1C) (said exerting of a pressuring force depicted as arrows pointing towards the deformable wall part). By doing so, the interior volume of the bottle part (1B) is compressed, thereby forcing the gaseous phase (3) at least partially out of the dropper bottle (1) through the optional drop brake channel (6) and the outflow channel (5).

In FIG. 4(C) the first pressuring force still exerted to the deformable wall part (1C), the dropper bottle (1) is inverted into an inverted position with the dropper mouth (7) pointing downwards and with the liquid composition contacting the outflow channel (5) and the optional drop brake channel (6), optionally partially filling the outflow channel (5) with the liquid ophthalmic composition (2).

In FIG. 4(D) the dropper bottle (1) is still in the inverted position and by releasing the first pressuring force from the deformable wall part (1C) (said release of the pressuring force depicted as arrows pointing away from the deformable wall part), air is sucked from the environment into the interior volume of the dropper bottle. The air and optionally the liquid composition (2) already in the outflow channel (5) sequentially flows through the outflow channel (5), and the optional drop brake channel (6) by force of the underpressure generated in the interior volume of the bottle part (1B).

FIG. 4(E) shows the situation in which by exerting a second pressuring force to the deformable wall part (1C) of the bottle part (1B) (said exerting of a pressuring force depicted as arrows pointing towards the deformable wall part), with the dropper bottle (1) still in the inverted (downside) position, the ophthalmic composition (2) is released from the dropper bottle (1) in a controlled dropwise manner. Upon release, the liquid ophthalmic composition (2) originating from the interior volume is sequentially flowing through the optional dropper brake channel (6) and the outflow channel (5), with the drops of the liquid composition to be released forming at the proximal end of the outflow channel (5), namely at the circular dropper mouth (7).

Figure 5:
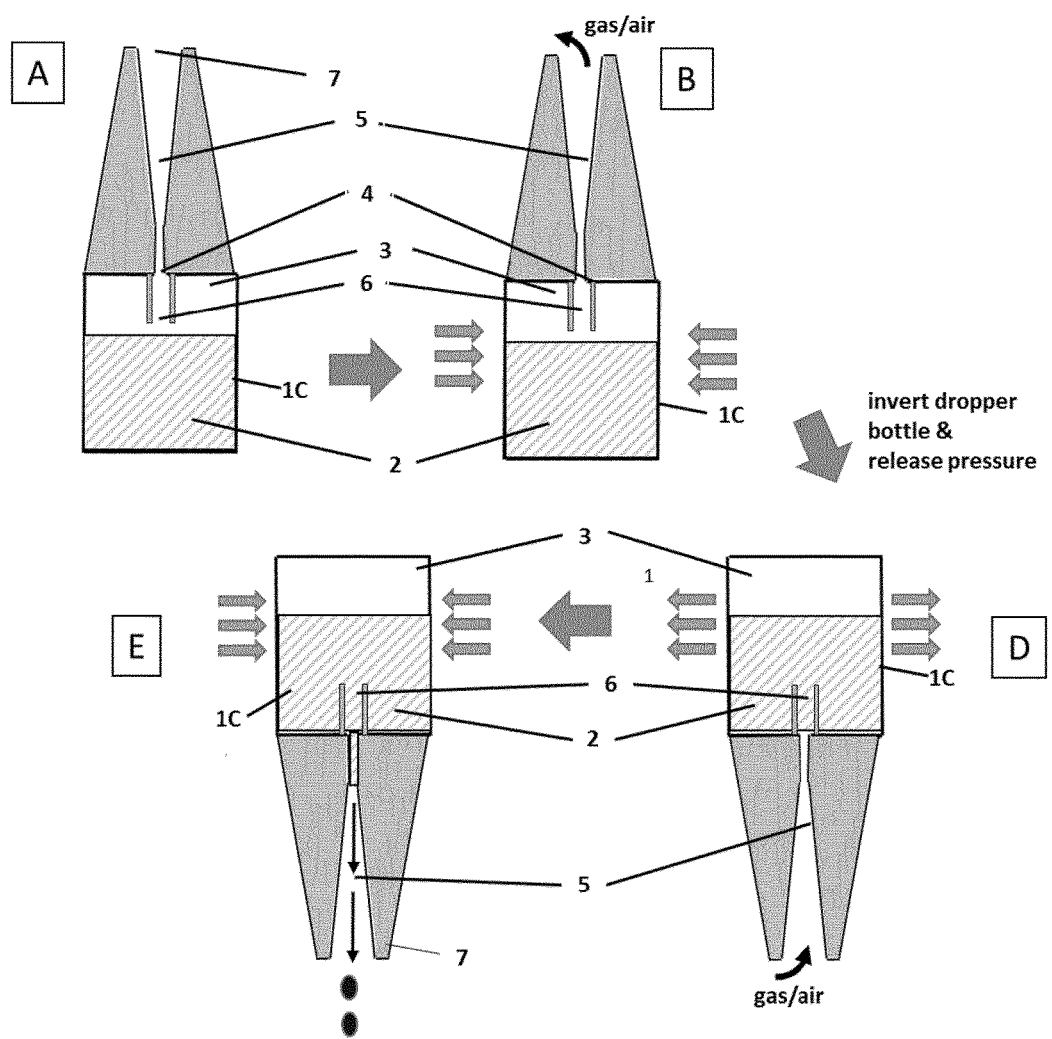
FIG. 5: Schematic representation of an embodiment of the method of the present invention

FIG. 5 is a schematic representation of an embodiment of the administration method of the present invention (underpressure method), wherein the inverting of the dropper bottle (1) into the inverted position (FIG. 3C) and the release of the pressuring force (FIG. 3D) is performed simultaneously. Thus, this embodiment of the present invention comprising sequentially the steps a) to e), wherein steps c) and d) are performed simultaneously:

FIG. 5(A) shows the starting position according to step a) of the method of the present invention. The dropper bottle (1) in the upright position, with no underpressure present in the interior volume of the bottle part (1B), the dropper mouth (7) pointing upwards.

FIG. 5(B) shows the situation in which a first pressurizing force is exerted to the deformable wall part of the bottle (1C) (said exerting of a pressuring force depicted as arrows pointing towards the deformable wall part). By doing so, the interior volume of the bottle part (1B) is reduced, thereby forcing the gaseous phase (3) at least partially out of the dropper bottle (1) into the environment, thereby sequentially flowing through the optional drop brake channel (6) and the outflow channel (5).

In FIG. 5(D) the dropper bottle (1) is shown in the inverted position after inversion and simultaneous release of said first pressuring force (said release of a pressuring force depicted as arrows pointing away from the deformable wall part), with the dropper mouth (7) pointing downwards and the liquid composition contacting the flow channel (5) and the optional drop brake channel (6). Air (and optionally the liquid composition (2) already in the outflow channel (5)) is sucked from the environment into the interior volume of the dropper bottle (1), by sequentially flowing through the outflow channel (5) and the optional drop brake channel (6), by force of the underpressure generated in the interior volume of the bottle part (1B).

FIG. 5(E) shows the situation in which by exerting a second pressuring force to the deformable wall part (1C) of the bottle part (1B) (said exerting of a pressuring force depicted as arrows pointing towards the deformable wall part), with the dropper bottle (1) still in the inverted position, the ophthalmic composition (2) is released from the dropper bottle (1) in a controlled drop-by-drop manner. Upon release, the liquid ophthalmic composition (2) originating from the interior volume is sequentially flowing through the optional dropper brake channel (6) and the outflow channel (5), with the drops forming at the proximal end of the outflow channel (5), namely at the (circular) dropper mouth (7).

Figure 6:
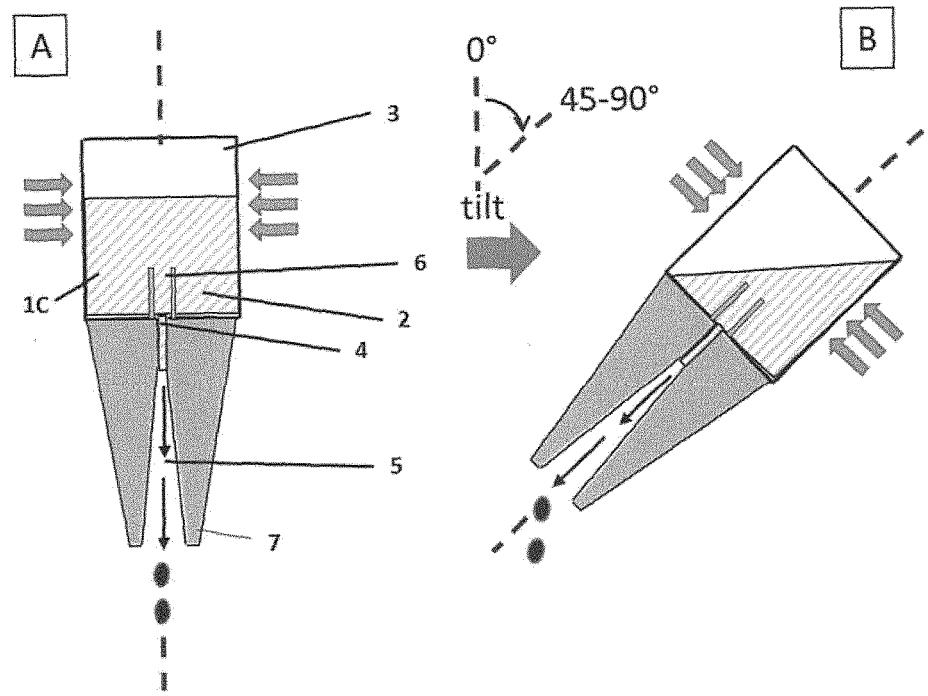
FIG. 6: Schematic representation of alternative inverted positions of a drop dispenser (1)

FIG. 6 is a schematic representation of alternative embodiments in which the drop dispenser or dropper bottle (1) is in the inverted position allowing controlled dropwise release of liquid ophthalmic compositions according to the administration method of the present invention.

In FIG. 6(A) a situation is shown in which by exerting a second pressuring force to the deformable wall part (1C) of the bottle part (1B) (said exerting of a pressuring force depicted as arrows pointing towards the deformable wall part), with the dropper bottle (1) in a fully inverted position the ophthalmic composition is released from the dropper bottle (1) in a controlled dropwise manner. (with the dropper mouth (7) pointing downwards and with the central axis of the dropper bottle (depicted as dashed line) being in an about perpendicular position and with the liquid composition (2) contacting the outflow channel (5).

FIG. 6 (b) shows a situation in which, by exerting a second pressuring force to the deformable wall part (1C) of the bottle part (1B) (said exerting of a pressuring force depicted as arrows pointing towards the deformable wall part), with the dropper bottle (1) in a tilted inverted position the ophthalmic composition is released from the dropper bottle in a controlled dropwise manner (with the dropper mouth (7) pointing downwards and with the central axis of the dropper bottle (depicted as dashed line) being in an about 45 to 90° angle in relation to the perpendicular position).

It is understood that according to the present invention the release of the liquid ophthalmic composition in a dropwise manner may be performed not only at said 2 exemplary positions depicted in FIG. 6(A) or 6(B), but also at all intermediate positions, namely at an angle of between 0° and up to 90° compared to a perpendicular axis.

Figure 7:
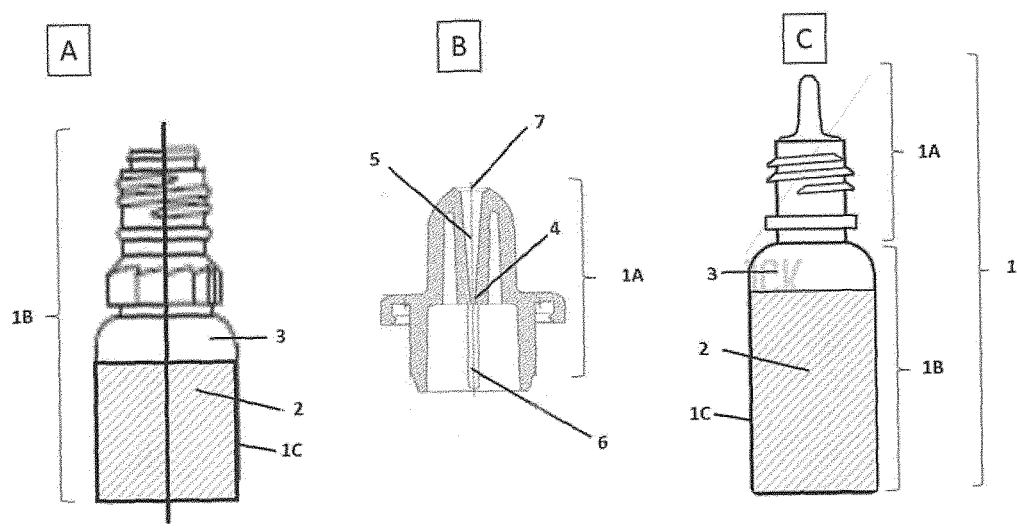
FIG. 7: Schematic representation of a drop dispenser (dropper bottle) (1) comprising a container part (bottle part) (1B) and a dropper part (1A)

FIG. 7 shows a schematic representation of a dropper bottle (1) comprising a bottle part (1B) and a dropper part (1A).

In FIG. 7(A) an exemplary bottle part (1B) is shown, comprising an interior volume that is at least partially filled with the liquid ophthalmic composition (2) and a gaseous phase (3) filing the remainder of the interior volume of the bottle part (1B). The wall of the bottle part is deformable (1C) as to allow a pressuring force (e.g. manual squeezing) to compress the interior volume.

FIG. 7(B) shows an exemplary dropper part (1A) comprising sequentially from its distal to its proximal end a drop brake channel (6) and an outflow channel (5), being in fluid communication with each other, with the outflow channel (5) being delimited at its distal end by the duct opening (4) and by the dropper mouth (7) at its proximal end.

FIG. 7(C) shows an exemplary dropper bottle (1) comprising said dropper part (1A) mounted onto the bottle part (1B).

Figure 8:
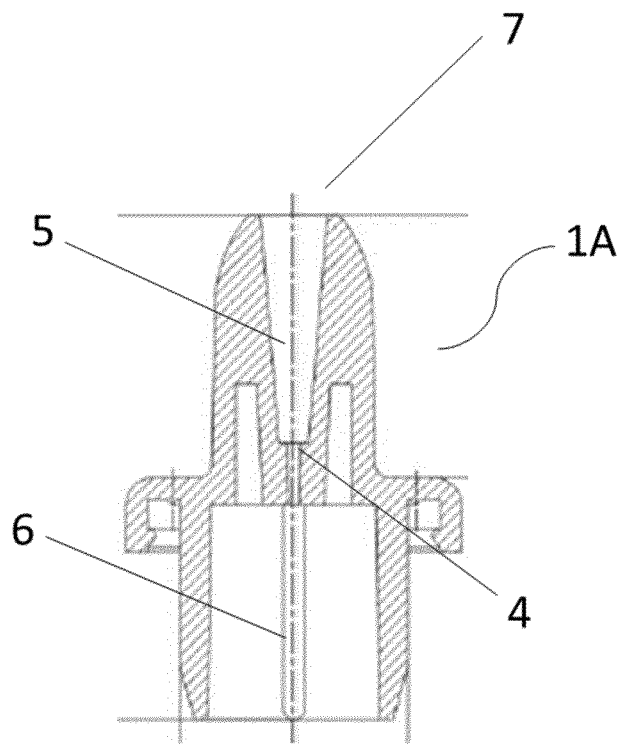
FIG. 8: Schematic representation of a dropper part (1A) of a drop dispenser (dropper bottle)

FIG. 8 shows another exemplary dropper part (1A) comprising sequentially from its distal to its proximal end a drop brake channel (6) and an outflow channel (5), being in fluid communication with each other, with the outflow channel (5) being delimited at its distal end by the duct opening (4) and by the dropper mouth (7) at its proximal end. In this particular embodiment, the duct opening (4) has a small inner diameter of, e.g. 0.15 mm and the outflow channel has a larger inner diameter which is increasing towards the dropper mouth (7), i.e. the proximal end of the outflow channel (5) to a diameter e.g. in the rage of 2.0 to 2.4 mm.

The following examples serve to illustrate the present invention without, however, limiting it in any respect:

EXAMPLES

Example 1: NovaTears® Ophthalmic Composition

The liquid NovaTears® (Novaliq GmbH, Germany) ophthalmic composition for treating dry eye disease, comprises 1-Perfluorohexyloctane (F6H8) and is provided in a dropper bottle (1) with a polyethylene dropper part (1A) mounted to a polypropylene bottle part (1B) for holding 3 ml of NovaTears®. The dropper part (1A) comprises an outflow channel (5) with a dropper mouth (7) (diameter 2.4 mm) at its proximal end and a duct opening (4) (0.3 mm diameter) at its distal end. The dropper part (1A) further comprises a dropper brake channel (6) which extends the outflow-channel (5) from the duct opening (4) into the interior volume of the bottle part (1B). The outflow channel (5) and the dropper brake channel (6) are in fluid communication with the interior volume of the bottle part (1B), allowing—upon inverting of the dropper bottle (1)—the liquid ophthalmic composition to flow from the interior volume to the proximal end of the outflow channel (5). Herein, the liquid first fills the optional drop brake channel (6), before it enters into the outflow channel (5) at the duct opening (4) and continues to the dropper mouth (7), where it is released as a drop.

Example 2: Administration of a SFA-Comprising Ophthalmic Composition (NovaTears®) Employing the Inversion Method After opening the dropper bottle (1), the subjects head is slightly tilted back, while looking upward. The lower eyelid is gently pulled downward, before the dropper bottle (1) is positioned with the dropper part (1A) above the lower eyelid. The dropper bottle is then inverted with the dropper mouth (7) facing to the eye of the subject. By doing so, drops are instantly released in an uncontrolled manner from the dropper mouth (7). Dropping starts unintentionally with drops being released in medium frequency. Dropping of the bottle can only be stopped by reverting the bottle back to the starting position.

Example 3: Administration of a SFA-Comprising Ophthalmic Composition (NovaTears®) Employing the Pressure Method After opening the dropper bottle (1), the subjects head is slightly tilted back, while looking upward. The lower eyelid is gently pulled downward, before the dropper bottle (1) is positioned with the dropper part (1A) above the lower eyelid. The dropper bottle (1) is then inverted with the dropper mouth (7) facing to the eye of the subject and then the deformable wall part (1C) of the bottle part (1B) is slightly squeezed by hand. By doing so, drops are instantly released in an uncontrolled manner from the dropper mouth (7). Dropping starts unintentionally with drops being released in high frequency. Dropping of the bottle can only be stopped by releasing the pressure force and reverting the bottle back to the starting position.

Example 4: Administration of a SFA-Comprising Ophthalmic Composition (NovaTears®) Employing the Method of the Present Invention (Underpressure Method)

After opening the dropper bottle (1), the subjects head is slightly tilted back, while looking upward your head back and look upward. The lower eyelid is gently pulled downward, before the dropper bottle (1) is positioned with the dropper part (1A) above the lower eyelid. While still in the upright position the deformable wall part (1C) of the bottle part (1B) of the dropper bottle (1) is slightly squeezed to force some of the gaseous volume in the headspace of the bottle part (1B) out of the dropper bottle (1). Then, the dropper bottle (1) is inverted (with the dropper mouth (7) facing down to the eye) and simultaneously the pressure is released from the deformable wall part (1C), thereby generating an underpressure inside the interior volume of the dropper bottle (1). Concomitantly, air from the environment is sucked through the outflow channel (5) into the interior volume. The underpressure generated prevents unintentional or uncontrolled release of drops from the dropper bottle (1). The controlled release of the composition in a drop-by-drop manner is initiated only when a second pressuring force is applied to the deformable wall part (1C). Hereby, the number of drops to be released is easily controlled by the second pressuring force. The dropping can be easily stopped by release of said second pressuring force and re-initiated by re-applying one or more further pressuring forces to the deformable wall part (1B) of the dropper bottle (1). Following the steps above, the NovaTears® ophthalmic composition is administered reliably to patients suffering from dry eye disease (keratoconjunctivitis sicca).

Example 5: Administration of an Ophthalmic Composition Comprising a SFA and an Active Pharmaceutical Ingredient Employing the Method of the Present Invention (Underpressure Method)

The liquid ophthalmic composition for treating dry eye disease, comprising 1 mg/ml Ciclosporine A, dissolved in 1 wt-% ethanol in 1-Perfluorobutyl-pentane (F4H5) is provided in a dropper bottle (1) with a polyethylene dropper part (1A) mounted to a polypropylene bottle part (1B).

Said cyclosporine-containing ophthalmic SFA-based-composition (3) is administered as described in Example 4. Herein, the underpressure generated prevents unintentional or uncontrolled release of drops of the pharmaceutical composition from the dropper bottle (1). The controlled release of the composition in a drop-by-drop manner is initiated only when a second pressuring force is applied to the deformable wall part (1C). Hereby, the number of drops to be released is easily controlled by said second pressuring force. The dropping of the pharmaceutical composition can be easily stopped by release of said second pressuring force and re-initiated by re-applying one or more further pressuring forces to the deformable wall part (1B) of the dropper bottle (1). Following the steps above, the ciclosporine-containing ophthalmic composition is administered reliably to patients suffering from dry eye disease (keratoconjunctivitis sicca).

Example 6: Parallel Testing of Different Liquid Ophthalmic Compositions and Dropper Bottles In the following, the administration method of the present invention (underpressure method) is compared to the inversion method. Herein, different liquid ophthalmic compositions and different dropper bottle configurations were tested when using either the underpressure method or the inversion method Experimental Procedure for the Underpressure Method (According to the Present Invention):

A dropper bottle (1) as listed in Table 1 below was provided and filled with a liquid ophthalmic composition as identified in Table 2. Then the sidewalls as the deformable wall part (1C)) of the dropper bottle (1) were slightly squeezed to force the gaseous phase (3) partially out of the dropper bottle (1). Afterwards, the bottles were inverted manually to an inverted position. During or after inversion of the dropper bottles the squeezing was stopped and the pressuring force was released, concomitantly generating underpressure in the inner volume of the dropper bottle (1). Finally, the inverted drop bottles were mounted on a suitable bottle holder at a fixed inclination versus the perpendicular axis. During a period of 30 seconds it was observed if drops are unintentionally released in an uncontrolled fashion without applying a second pressuring force to the deformable wall part of the bottle and the number of drops released were recorded.

Experimental Procedure for the Inversion Method (not According to the Present Invention):

A dropper bottle (1) as listed in Table 1 below was provided and filled with a liquid ophthalmic composition as identified in Table 2. Then the dropper bottles were inverted manually to an inverted position. Finally, the inverted drop bottles were mounted on a suitable bottle holder at a fixed inclination versus the perpendicular axis. During a period of 30 seconds it was observed if drops are unintentionally released in an uncontrolled fashion without applying a second pressuring force to the deformable wall part of the bottle and the number of drops released were recorded. Table 1: Dropper bottle configurations as employed in Example 6:

| dropper type | dropper, manufacturer | bottle part (1B) | dropper part (1A) | diameter dropper mouth opening (7)/mm | diameter duct opening (4)/mm | dropper brake channel (6) |
|---|---|---|---|---|---|---|
| 1 | Packsys GmbH | polypropylene | polyethylene | 2.4 | 0.3 | yes |
| 2 | Packsys GmbH | polyethylene | polyethylene | 2.4 | 0.3 | yes |
| 3 | Packsys GmbH | polypropylene | polyethylene | 2.4 | 0.8 | no |
| 4 | Packsys GmbH | polypropylene | polyethylene | 2.4 | 1.2 | no |
| 5 | Packsys GmbH | polypropylene | polyethylene | 2.4 | 0.2 | yes |
| 6 | Systane ® dropper | n.d. | n.d. | n.d. | n.d. | yes |
| 7 | Artelac ® dropper (Bausch + Lomb) | n.d. | n.d. | n.d. | n.d. | yes |
| 8 | Refresh ® by Artelac ® dropper | n.d. | n.d. | n.d. | n.d. | yes |
| 9 | Thealoz ® Abak* | n.d | n.d. | n.d. | n.d. | n.d. |
| 10 | Nemera Novelia ®** | n.d | n.d. | n.d. | n.d. | n.d. |

TABLE 2

| Solvent | Formulation type | API, excipients | dropper type | duct opening diameter/mm | release of first pressuring force | dropping angle | inversion method successful | underpressure method successful |
|---|---|---|---|---|---|---|---|---|
| F6H8 | solution | n.a. | 1 | 0.3 | after inversion | 0° | no | yes |
| F6H8 | solution | n.a. | 1 | 0.3 | after inversion | tilted (45°) | no | yes |
| F4H5 | solution | n.a. | 1 | 0.3 | after inverting | 0° | no | yes |
| F4H5 | solution | n.a. | 1 | 0.3 | after inversion | tilted (45°) | no | yes |
| F4H5 | solution | cyclosporin (0.1% w/v), ethanol (1% w/w) | 1 | 0.3 | after inversion | 0° | no | yes |
| F4H5 | solution | cyclosporin (0.1% w/v), ethanol (1% w/w) | 1 | 0.3 | after inversion | tilted (45°) | no | yes |
| F6H8 | solution | n.a. | 1 | 0.3 | during inversion | 0° | no | yes |
| F6H8 | solution | n.a. | 1 | 0.3 | during inversion | tilted (45°) | no | yes |
| F6H8 | solution | n.a. | 2 | 0.3 | during inversion | 0° | no | yes |
| F6H8 | solution | n.a. | 2 | 0.3 | during inversion | tilted (45°) | no | yes |
| F6H8 | solution | n.a. | 2 | 0.3 | during inversion | tilted (45°) | no | yes |
| F4H5 | solution | n.a. | 3 | 0.8 | during inversion | 0° | no | yes |
| F4H5 | solution | n.a. | 4 | 1.2 | during inversion | 0° | no | yes |
| water | solution | n.a. | 4 | 1.2 | during inversion | 0° | (yes) | yes |
| F4H5 | suspension | sucrose (0.025% w/w) | 1 | 0.3 | during inversion | 0° | n.a. | yes |
| ethanol | solution | n.a. | 5 | 0.2 | during inversion | 0° | (yes) | yes |
| F4H5 | solution | cyclosporin (0.1 % w/v), ethanol (1% w/w) | 5 | 0.2 | during inversion | 0° | no | yes |

TABLE 2-continued

| Solvent | Formulation type | API, excipients | dropper type | duct opening diameter/mm | release of first pressuring force | dropping angle | inversion method successful | underpressure method successful |
|---|---|---|---|---|---|---|---|---|
| water | solution | Systane ® (commercial eye drops) | 6 | n.a. | during inversion | 0° | (yes) | yes |
| water | solution | Artelac ® (commercial eye drops) | 7 | n.a. | during inversion | 0° | no | yes |
| F4H5 | solution | n.a. | 6 | n.a. | during inversion | 0° | no | yes |
| F4H5 | solution | n.a. | 7 | n.a. | during inversion | 0° | no | yes |
| Propyl-ethylen-glycol | solution | | 5 | 0.2 | during inversion | 0° | no | no |
| water | solution | Refresh ® (commercial eye drops) | 8 | n.a. | during inversion | 0° | no | yes |
| F6H8 | solution | n.a. | 8 | n.a. | during inversion | 0° | no | yes |
| water | solution | Thealoz ® Duo (commercial eye drops) | 9 | n.a. | during inversion | 0° | yes | yes |
| water | solution | Thealoz ® Duo (commercial eye drops) | 9 | n.a. | after inversion | 0° | yes | yes |
| F4H5 | solution | n.a. | 10 | n.a. | during inversion | 0° | yes | yes |
| F4H5 | solution | n.a. | 10 | n.a. | after inversion | 0° | yes | yes |
| F4H5 | solution | n.a. | 1 | 0.3 | during inversion | 0° | no | yes |
| F4H5 | solution | n.a. | 1 | 0.3 | during inversion | 90° | no | yes |
| F4H5 | solution | n.a. | 1 | 0.3 | after inversion | 0° | no | yes |
| F4H5 | solution | n.a. | 1 | 0.3 | after inversion | 90° | no | yes |

Herein, the inversion method or the underpressure method were considered successful ("yes") when no drops within 30 seconds were unintentionally released from the dropper mouth (7) of the dropper bottle in an uncontrolled fashion without any pressure applied to the deformable wall part (1C) of the dropper bottle (1). Further, "(yes)" in brackets refers to only one drop unintentionally released within said 30 second observation period.

Example 7: Testing the Underpressure Method with Different Volumes and Temperatures According to the protocols as described under example 6 above for the inversion method and the underpressure method, respectively, further measurements were carried out at 21° C. and 5° C. with increasing gaseous phase (3) (headspace volume) in the interior volume of the dropper bottle (1). The results are listed in Table 3:

TABLE 3

| Solvent | Formulation type | dropper type | temperature/° C. | composition volume/ml | inversion method successful | underpressure method successful |
|---|---|---|---|---|---|---|
| F6H8 | solution | 1 | 21 | 5 | no | yes |
| F6H8 | solution | 1 | 21 | 4 | no | yes |
| F6H8 | solution | 1 | 21 | 3 | no | yes |
| F6H8 | solution | 1 | 21 | 2 | no | yes |
| F6H8 | solution | 1 | 21 | 1 | no | yes |
| F6H8 | solution | 2 | 21 | 5 | no | yes |
| F6H8 | solution | 2 | 21 | 4 | no | yes |
| F6H8 | solution | 2 | 21 | 3 | no | yes |
| F6H8 | solution | 2 | 21 | 2 | no | yes |
| F6H8 | solution | 2 | 21 | 1 | no | yes |
| F6H8 | solution | 1 | 5 | 5 | no | yes |
| F6H8 | solution | 1 | 5 | 4 | no | yes |
| F6H8 | solution | 1 | 5 | 3 | no | yes |
| F6H8 | solution | 1 | 5 | 2 | no | yes |
| F6H8 | solution | 1 | 5 | 1 | no | yes |
| F6H8 | solution | 2 | 5 | 5 | no | yes |
| F6H8 | solution | 2 | 5 | 4 | no | yes |
| F6H8 | solution | 2 | 5 | 3 | no | yes |
| F6H8 | solution | 2 | 5 | 2 | no | yes |
| F6H8 | solution | 2 | 5 | 1 | no | yes |

Herein, the inversion method or the underpressure method were considered successful ("yes") when no drops within 30 seconds were unintentionally released from the dropper mouth (7) of the dropper bottle in an uncontrolled fashion without any pressure applied to the deformable wall part (1C) of the dropper bottle (1). Further, "(yes)" in brackets refers to only one drop unintentionally released within said 30 second observation period.

Example 8: Comparative Drop Size Analysis of Polypropylene Drop Dispenser with Different Outflow Channel Diameters Filled with F6H8 at Different Fill Levels Three polypropylene droppers (Packsys®) with a duct opening diameter of 0.3 mm and a mouth diameter of 2.4 mm ("Dropper 14182") were filled with 1 ml, 3 ml and 5 ml of F6H8. Prior to testing the bottles were closed with dropper and cap. The cap was removed and sample fluid F6H8 was dispensed dropwise. 5 drops of F6H8 were collected from the start, middle and end of each sample (5 ml; 3 ml; 1 ml respectively) were weighed and the corresponding drop sizes calculated on the basis of the density of F6H8 (1.331 gcm$^{-3}$). Table 4 shows the resulting average drop weights and volumes:

TABLE 4

| Dropper 14182 | F6H8 | | | |
|---|---|---|---|---|
| | 5 mL | 3 mL | 1 mL | Average |
| Average Drop Weight (mg) | 14.967 | 15.458 | 15.035 | 15.153 |
| % RSD of Drop Weight | 0.940 | 0.873 | 1.061 | 0.964 |
| Average Drop Volume (μL) | 11.245 | 11.614 | 11.296 | 11.385 |
| % RSD of Drop Size | 0.706 | 0.656 | 0.797 | 0.725 |

The experiment was repeated using three polypropylene droppers (Packsys®) with a duct opening diameter of 0.15 mm and a mouth diameter of 2.4 mm ("Dropper 14014"). Table 5 shows the resulting average drop weights and volumes:

TABLE 5

| Dropper 14014 | F6H8 | | | |
|---|---|---|---|---|
| | 5 mL | 3 mL | 1 mL | Through-Life |
| Average Drop Weight (mg) | 14.509 | 14.540 | 14.498 | 14.516 |
| % RSD of Drop Weight | 0.646 | 0.760 | 0.699 | 0.687 |
| Average Drop Volume (μL) | 10.901 | 10.924 | 10.893 | 10.906 |
| % RSD of Drop Size | 0.486 | 0.571 | 0.525 | 0.516 |

Table 6 shows the drop weights in mg as measured for the three droppers, each having a duct opening diameter of 0.3 mm and a mouth diameter of 2.4 mm (Dropper 14182).

TABLE 6

| Fill | 14182 F6H8 Drop Weight (mg) | | |
|---|---|---|---|
| Volume | 1 | 2 | 3 |
| 5 mL | 15.260 | 16.089 | 14.115 |
| | 13.397 | 15.257 | 13.251 |
| | 15.168 | 15.620 | 16.119 |
| | 14.873 | 14.525 | 16.155 |
| | 14.105 | 14.813 | 15.753 |
| 3 mL | 15.693 | 14.928 | 17.034 |
| | 15.739 | 15.120 | 16.204 |
| | 14.668 | 14.648 | 16.424 |
| | 15.949 | 14.665 | 16.584 |
| | 15.058 | 13.855 | 15.295 |
| 1 mL | 14.637 | 15.426 | 16.599 |
| | 14.877 | 13.054 | 16.255 |
| | 13.947 | 14.200 | 13.827 |
| | 15.543 | 14.526 | 16.084 |
| | 16.526 | 14.572 | 15.451 |

Table 7 shows the comparison of the drop sizes generated with droppers having a duct opening of either 0.3 mm or 0.15 mm. As can be seen, a smaller diameter of the duct opening helps to adjust the drop volume to a target drop volume of 10,11. Furthermore, a smaller duct opening allows to realize more constant drop volumes, independent from the fill level of the dropper bottle used.

TABLE 7

| | Material: F6H8 | | | |
|---|---|---|---|---|
| | 5 mL | 3 mL | 1 mL | Average |
| 14182 Average Drop Volume (μL) | 11.245 | 11.614 | 11.296 | 11.385 |
| 14182 % RSD of Drop Size | 0.706 | 0.656 | 0.797 | 0.725 |
| 14014 Average Drop Volume (μL) | 10.901 | 10.924 | 10.893 | 10.906 |
| 14014 % RSD of Drop Size | 0.486 | 0.571 | 0.525 | 0.516 |

Example 9: Testing of a Polypropylene Drop Dispenser with a Duct Opening Diameter of 0.15 mm at Reduced Temperature at 5° C. with F4H5 and F6H8

A drop dispenser (Packsys GmbH) with a volume of 5 ml, a duct opening with a diameter of 0.15 mm and a dropper mouth with a diameter of 2.4 mm was tested at 5° C. with F4H5 and F6H8 at different volumes.

Three of the above-described polypropylene dropper bottles were filled with different volumes of F4H5 and F6H8 (5 ml; 3 ml; 1 ml). Prior to testing, the bottles were closed with dropper and cap; then stored over night at 5° C. This was repeated with the three bottles containing each material.

Without pressing the bottle was automatically inverted by 180° for 30 seconds. Drop formation of F4H5 or F6H8 and release was observed on blue paper and counted. For data analysis purposes any droplet that failed to drop but was observed was counted as a drop. Table 8 shows the number of drops observed.

TABLE 8

| Fill | F4H5 | | | F6H8 | | |
|---|---|---|---|---|---|---|
| Volume | 1 | 2 | 3 | 1 | 2 | 3 |
| 5 mL | 0 | 0 | 0 | 0 | 0 | 0 |
| 3 mL | 2 | 3 | 2 | 0 | 1 | 1 |
| 1 mL | 2 | 2 | 1 | 1 | 2 | 2 |

Furthermore, 5 drops of each SFA was collected from each of the 3 parallel drop dispensers from the start, middle and end of each sample (5 ml; 3 ml; 1 ml respectively), weighed and the drop size calculated on the basis of the respective density (F4H5, 1.29 g/cm$^3$; F6H8, 1.331 g/cm$^3$). Table 9 shows the drop sizes observed for each of the 3 drop dispensers tested in parallel.

TABLE 9

| Fill | F4H5 Drop Weight (mg) | | | F6H8 Drop Weight (mg) | | |
|---|---|---|---|---|---|---|
| Volume | 1 | 2 | 3 | 1 | 2 | 3 |
| 5 mL | 14.209 | 13.560 | 13.998 | 15.391 | 15.448 | 15.265 |
| | 15.132 | 13.543 | 13.160 | 15.078 | 15.406 | 16.189 |
| | 14.408 | 12.940 | 15.184 | 14.308 | 15.406 | 16.092 |
| | 13.724 | 12.989 | 13.177 | 15.714 | 16.137 | 15.987 |
| | 12.268 | 13.932 | 13.449 | 14.587 | 15.864 | 15.310 |

TABLE 9-continued

| Fill Volume | F4H5 Drop Weight (mg) | | | F6H8 Drop Weight (mg) | | |
|---|---|---|---|---|---|---|
| | 1 | 2 | 3 | 1 | 2 | 3 |
| 3 mL | 12.881 | 14.085 | 13.914 | 15.749 | 15.819 | 15.696 |
| | 15.184 | 12.648 | 14.611 | 12.865 | 15.067 | 15.597 |
| | 13.935 | 13.912 | 14.462 | 15.587 | 14.946 | 16.227 |
| | 13.287 | 12.881 | 13.411 | 14.672 | 15.383 | 15.440 |
| | 13.176 | 13.687 | 14.569 | 15.909 | 15.022 | 15.446 |
| 1 mL | 14.651 | 13.984 | 14.068 | 15.845 | 13.675 | 13.202 |
| | 13.519 | 13.997 | 13.428 | 15.345 | 15.501 | 15.472 |
| | 13.473 | 14.600 | 13.841 | 15.019 | 15.541 | 15.680 |
| | 13.211 | 10.317 | 13.176 | 15.501 | 13.537 | 14.010 |
| | 12.102 | 13.885 | 12.675 | 14.160 | 14.996 | 14.869 |

Table 10 shows the average weights as well as the average volumes of the observed drops.

TABLE 10

| Summary | F4H5 | | | | F6H8 | | | |
|---|---|---|---|---|---|---|---|---|
| | 5 ml | 3 ml | 1 ml | Average | 5 ml | 3 ml | 1 ml | Average |
| Average Drop Weight (mg) | 13.712 | 13.776 | 13.395 | 13.628 | 15.479 | 15.295 | 14.824 | 15.199 |
| % RSD of Drop Weight | 0.800 | 0.734 | 1.082 | 0.881 | 0.547 | 0.786 | 0.873 | 0.783 |
| Average Drop volume (µl) | 10.629 | 10.679 | 10.384 | 10.564 | 11.629 | 11.491 | 11.137 | 11.419 |
| % RSD of Drop size | 0.620 | 0.569 | 0.839 | 0.683 | 0.411 | 0.591 | 0.656 | 0.588 |

Example 10: Testing of a Polypropylene Drop Dispenser with a Duct Opening Diameter of 0.15 Mm Filled with F6H8 at Different Filling Levels In this experiment 3 series of 5 polypropylene droppers with a duct opening diameter of 0.15 mm and a mouth diameter of 2.4 mm ("Dropper 14014") and a total volume of 5 ml were filled with F6H8 at different filling volumes: 5 droppers (droppers 1 to 5) were filled with 0.2 ml F6H8 each (filling level "nearly empty"); 5 droppers were filled with 3 ml F6H8 each (filling level "half full") and 5 droppers were filled with 5 ml F6H8 each (filling level "full") at room temperature. The dropper bottles were opened and inverted by 180° to a vertical orientation with the dropper mouth pointing downwards. For a period of 10 s it was observed whether the spontaneous formation of drops occurred. The drops, if formed, were counted. Table 11 summarizes the results of the experiment with "OK" depicting that no drops were formed within 10 s from the inversion of the bottle.

TABLE 11

| Dropper | Filling volume 0.2 ml (nearly empty) | Filling volume 3 ml (half full) | Filling volume 5 ml (full) |
|---|---|---|---|
| 1 | OK | OK | OK |
| 2 | OK | OK | OK |
| 3 | OK | OK | OK |
| 4 | OK | OK | OK |
| 5 | OK | OK | OK |

The invention claimed is:
1. A method for dropwise topical administration of a liquid composition (2), comprising the steps of:
   a) providing a drop dispenser (1), comprising:
      a container part (1B) with an interior volume partially filled with the liquid composition (2) and a gaseous phase (3) filling the remainder of the interior volume at ambient pressure, the container part (1B) having a displaceable section (1C) and optionally a substantially stationary section, and
      a dropper part (1A) in physical connection and in fluid communication with the interior volume of the container part (1B), comprising an outflow channel (5), connecting the interior volume of the container part (1B) to the environment;
   b) exerting a first force to the displaceable section (1C) of the container part (1B) of the drop dispenser (1) while holding the drop dispenser (1) in an upright position in which the outflow channel (5) is not in contact with the liquid composition (2), thereby reducing the interior volume of the container part (1B) and forcing the gaseous phase (3) of the interior volume at least partially out of the drop dispenser (1) into the environment;
   c) inverting the drop dispenser (1) to an inverted position in which the liquid composition (2) is in contact with the outflow channel (5);
   d) releasing said first force from the displaceable section (1C) of the container part (1B) at least partly, thereby reducing the pressure inside the container part (1B) below ambient pressure; and
   e) exerting a second force to the displaceable section (1C) of the container part (1B), while still holding the drop dispenser in the inverted position in which the liquid composition (2) is in contact with the outflow channel (5), thereby raising the pressure inside the interior volume of the container part (1B) above ambient pressure and releasing the liquid composition (2) dropwise from the dropper part (1A) of the drop dispenser (1).
2. The method according to claim 1, wherein the drop dispenser (1) is a dropper bottle with a dropper part (1A) and a container part (1B), the container part (1B) comprising the displaceable section (1C).
3. The method according to claim 1, wherein the inversion of the drop dispenser (1) to the inverted position according to step (c) and the release of the first force according to step (d) is performed at least partly simultaneously.

4. The method according to claim 1, wherein the liquid composition (2) is an ophthalmic composition.

5. The method according to claim 1, wherein the liquid composition (2) comprises a liquid semifluorinated alkane.

6. The method according to claim 1, wherein the liquid composition (2) further comprises water.

7. The method according to claim 1, wherein the reduced pressure generated inside the interior volume of the container part (1B) prevents unintended release of the liquid composition (2).

8. The method according to claim 1, wherein the liquid composition (2) has a density measured at 25° C. in the range of 1.0 to 1.7 g/cm$^3$.

9. The method according to claim 1, wherein the liquid composition (2) has a viscosity measured at 25° C. in air in the range of 0.9 to 4.0 mPa s.

10. The method according to claim 1, wherein the liquid composition (2) has a surface tension in air measured at 25° C. in the range of 15 to 30 mN/m.

11. The method according to claim 1, wherein the liquid composition (2) comprises a liquid linear or branched semifluorinated alkane having one perfluorinated segment and one non-fluorinated hydrocarbon segment.

12. The method according to claim 1, wherein the liquid composition (2) further comprises one or more pharmaceutical active ingredients.

13. The method according to claim 1, further comprising the step:
   f) dropwise administering the composition to the eye, eye lid, eye sac or an ophthalmic tissue of a subject in need thereof.

14. A method of treating an ocular disease or disorder, or any symptoms or conditions associated therewith, comprising dropwise administration of a liquid ophthalmic composition according to the method of claim 1.

15. The method according to claim 14, wherein the ocular disease or disorder is dry eye disease.

16. The method according to claim 14, wherein the ocular disease or disorder is a disease or disorder of the eyelid, lacrimal system, orbit, conjunctiva, sclera, cornea, iris, ciliary body, lens, choroid and/or retina.

17. The method according to claim 11, wherein each segment independently has a number of carbon atoms selected from the range of 3 to 10.

\* \* \* \* \*